US009416150B2

(12) United States Patent
Bergmann et al.

(10) Patent No.: US 9,416,150 B2
(45) Date of Patent: Aug. 16, 2016

(54) IRIDIUM-BASED COMPLEXES FOR ECL

(71) Applicant: Roche Diagnostics Operations, Inc., Indianapolis, IN (US)

(72) Inventors: Frank Bergmann, Iffeldorf (DE); Robert Cysewski, Chojnice (PL); Luisa de Cola, Strasbourg (FR); Sebastian Dziadek, Benediktbeuern (DE); Jesus Miguel Fernandez Hernandez, Murcia (ES); Hans-Peter Josel, Weilheim (DE); Christoph Seidel, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/609,649

(22) Filed: Jan. 30, 2015

(65) Prior Publication Data
US 2015/0147751 A1    May 28, 2015

Related U.S. Application Data

(63) Continuation of application No. PCT/EP2013/002323, filed on Aug. 2, 2013.

(30) Foreign Application Priority Data

Aug. 2, 2012  (EP) .................................... 12179054

(51) Int. Cl.
| | | |
|---|---|---|
| C07F 15/00 | (2006.01) | |
| G01N 33/58 | (2006.01) | |
| C09K 11/06 | (2006.01) | |
| C09K 11/07 | (2006.01) | |

(52) U.S. Cl.
CPC ............. *C07F 15/0033* (2013.01); *C09K 11/06* (2013.01); *C09K 11/07* (2013.01); *G01N 33/582* (2013.01); *C09K 2211/1007* (2013.01); *C09K 2211/1029* (2013.01); *C09K 2211/14* (2013.01); *C09K 2211/1408* (2013.01); *C09K 2211/1416* (2013.01); *C09K 2211/1425* (2013.01); *C09K 2211/1441* (2013.01); *C09K 2211/1466* (2013.01); *C09K 2211/185* (2013.01)

(58) Field of Classification Search
CPC .......................... C07F 15/0033; G01N 33/582
See application file for complete search history.

(56) References Cited

U.S. PATENT DOCUMENTS

| | | | |
|---|---|---|---|
| 5,219,847 A | 6/1993 | Taguchi et al. | |
| 7,067,202 B2 * | 6/2006 | Fujii ................... | C07F 15/0033 313/504 |
| 2004/0091738 A1 | 5/2004 | Psai et al. | |
| 2004/0134461 A1 | 7/2004 | Bishop | |
| 2004/0239237 A1 | 12/2004 | Matsusue et al. | |
| 2006/0134461 A1 | 6/2006 | Huo et al. | |
| 2006/0237714 A1 | 10/2006 | Park et al. | |
| 2006/0263630 A1 | 11/2006 | Ho et al. | |
| 2007/0015005 A1 | 1/2007 | Chen et al. | |
| 2007/0087221 A1 | 4/2007 | Wu et al. | |
| 2007/0141394 A1 | 6/2007 | Cheng et al. | |
| 2008/0217606 A1 | 9/2008 | Cheng et al. | |
| 2008/0299414 A1 | 12/2008 | Watanabe et al. | |

FOREIGN PATENT DOCUMENTS

| | | |
|---|---|---|
| CN | 1397559 A | 2/2003 |
| CN | 1474826 A | 2/2004 |
| CN | 102604628 A | 7/2012 |
| DE | 102008063490 A1 | 6/2010 |
| EP | 0404097 B1 | 12/1990 |
| EP | 1418217 A1 | 5/2004 |
| EP | 2062959 A2 | 5/2009 |
| JP | 2007-169474 A | 7/2007 |
| WO | 93/01161 A1 | 1/1993 |
| WO | 03/063555 A1 | 7/2003 |
| WO | 2005/019373 A2 | 3/2005 |
| WO | 2005/118606 A1 | 12/2005 |
| WO | 2007/095118 A2 | 8/2007 |
| WO | 2008/096609 A1 | 8/2008 |
| WO | 2009/026235 A2 | 2/2009 |
| WO | 2009/050281 A1 | 4/2009 |
| WO | 2010/069442 A1 | 6/2010 |
| WO | 2010/069444 A1 | 6/2010 |
| WO | 2011/000616 A1 | 1/2011 |
| WO | 2011/067401 A1 | 6/2011 |

OTHER PUBLICATIONS

International Search Report issued Feb. 10, 2014 in Application No. PCT/EP2013/002323, 3 pages.
Cymerman, J. and Short, W. F., "150. Amidines. Part XII. Preparation of 9-substituted Phenanthridines from N-2-Diphenylylamidines," Journal of the American Chemical Society, 1949, pp. 703-707.
Holliger, Philipp et al., "'Diabodies': Small bivalent and bispecific antibody fragments," Proceedings of the National Academy of Sciences USA, Jul. 1993, pp. 6444-6448, vol. 90.
Hudson, Peter J. and Souriau, Christelle, "Engineered antibodies," Nature Medicine, Jan. 2003, pp. 129-134, vol. 9, No. 1.
Kohmoto, Shigeo et al., "Room-Temperature Discotic Nematic Liquid Crystals over a Wide Temperature Range: Alkali-Metal-Ion-Induced Phase Transition from Discotic Nematic to Columnar Phases," Journal of the American Chemical Society, 2007, pp. 13364-13365, vol. 129.
Lamansky, Sergey et al., "Synthesis and Characterization of Phosphorescent Cyclometalated Iridium Complexes," Inorganic Chemistry, 2001, pp. 1704-1711, vol. 40.
Lion, C. et al., "Synthesis in the Phenanthridine Series, I. Search for Optimum Experimental Conditions in the Preparation fo 6-Alkylphenanthridines and of the Salt Thereof," Bulletin des Sociétés Chimiques Belges, 1989, pp. 557-566, vol. 99, with English translation.
Nicolai, Eric et al., "Synthesis and Angiotension II Receptor Antagonist Activity of C-Linked Pyrazole Derivatives," Chemical and Pharmaceutical Bulletin, 1994, pp. 1617-1630, vol. 42, No. 8, Pharmaceutical Society of Japan.

(Continued)

*Primary Examiner* — Joseph Kosack
(74) *Attorney, Agent, or Firm* — Roche Diagnostics Operations, Inc.

(57) ABSTRACT

The present invention relates to novel iridium-based Ir(III) luminescent complexes, conjugates comprising these complexes as a label and their application, e.g. in the electrochemiluminescence based detection of an analyte.

11 Claims, No Drawings

(56) References Cited

OTHER PUBLICATIONS

Nonoyama, Matsuo, "Chelating C-metallation of N-Phenylpyrazole with Rhodium(III) and Iridium(III)," Journal of Organometallic Chemistry, 1975, pp. 263-267, vol. 86.

Plueckthun, A., "Chapter 11 Antibodies from *Escherichia coli*," The Pharmacology of Monoclonal Antibodies, 1994, pp. 269-315, vol. 113, Springer-Verlag, New York.

Youn, So Won and Bihn, Joon Hyung, "Trifluoroacetic acid-mediated facile construction of 6-substituted phenanthridines," Tetrahedron Letters, 2009, pp. 4598-4601, vol. 50.

Altuntas, Esra et al., Determination of the relative ligand-binding strengths in heteroleptic IrIII complexes by ESI-Q-TOF tandem mass spectrometry, Journal of Mass Spectrometry, 2012, pp. 34-40, vol. 47.

Dorwald, F. Zaragoza, Preface and 1.Organic Synthesis: General Remarks, Side Reactions in Organic Synthesis a Guide to Successful Synthesis Design, 2005, p. IX of Preface, pp. 1-15, Wiley-VCH, Weinheim, DE.

Hilpert, Hans, 118. Syntheses von 3-(2-Carboxy-4-pyridl)-und 3-(6-Carboxy-3-pyridl)-DL-alanin, Helvetica Chimica Acta, 1987, pp. 1307-1311, vol. 70.

Lee, Young Hee et al., Theoretical Study of Ir(III) Complexes of Fluorinated Phenylbenzoquinoline as Red Phosphorescent Material, Japanese Journal of Applied Physics, 2006, pp. 563-567, vol. 45, No. 1B.

Moderhack, Dietrich and Schneider, Jan-Christoph, A New Series of Non-classical Type C Heteropentalenes: 2H-Pyrrolo[2,1-c][1,2,4]triazoles, Journal of Heterocyclic Chemistry, 2007, pp. 393-401, vol. 44, No. 2.

\* cited by examiner

IRIDIUM-BASED COMPLEXES FOR ECL

CROSS REFERENCE TO RELATED APPLICATIONS

This application is a continuation of PCT/EP2013/002323 filed Aug. 2, 2013 and claims priority to EP Patent Application No. 12179054.7 filed Aug. 2, 2012, the disclosures of which are hereby incorporated by reference in their entirety.

BACKGROUND OF THE INVENTION

The present invention relates to novel iridium-based Ir(III) luminescent complexes, conjugates comprising these complexes as a label and their application, e.g. in the electrochemiluminescence based detection of an analyte.

Electrogenerated chemiluminescence (also called electrochemiluminescence and abbreviated ECL) is the process whereby species generated at electrodes undergo high-energy electron-transfer reactions to form excited states that emit light. The first detailed ECL studies were described by Hercules and Bard et al. in the mid-1960s. After about 50 years of study, ECL has now become a very powerful analytical technique and is widely used in the areas of, for example, immunoassay, food and water testing, and biowarfare agent detection.

There is a tremendous number of compounds that appears to be of interest for use in organic light emitting devices (OLEDs). These compounds are appropriate for use in solid materials or may be dissolved in organic fluids. However, no conclusion can be drawn regarding their utility in an aqueous medium as e.g., required for detection of an analyte from a biological sample.

In general ECL-based detection methods are based on the use of water-soluble ruthenium complexes, comprising Ru(II+) as metal ion.

Despite significant improvements made over the past decades, still a tremendous need exists for more sensitive electrochemiluminescence-based in vitro diagnostic assays.

It has now been surprisingly found that certain iridium-based Ir(III+) luminescent complexes, represent very promising labels for future high sensitive ECL-based detection methods.

SUMMARY OF THE INVENTION

The present invention discloses an iridium-based chemiluminescent compound of Formula I

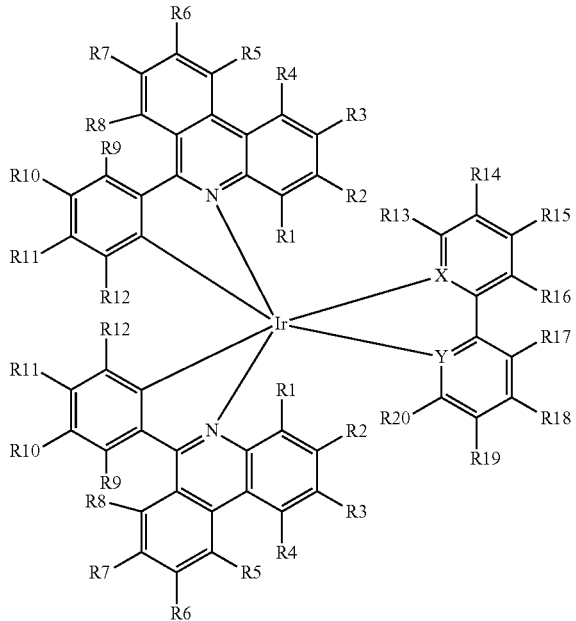

wherein each R1-R20 independently is hydrogen, halide, cyano- or nitro-group, amino, substituted amino, alkylamino, substituted alkylamino, arylamino, substituted arylamino, alkylammonium, substituted alkylammonium, carboxy, carboxylate, carboxylic acid ester, carbamoyl, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl, sulfoxide, phosphono, hydroxyphosphinoyl, hydroxy-alkyl-phosphinoyl, phosphonate, phosphinate or R21, wherein R21 is aryl, substituted aryl, alkyl, substituted alkyl, branched alkyl, substituted branched alkyl, arylalkyl, substituted arylalkyl, alkylaryl, substituted alkylaryl, alkenyl, substituted alkenyl, alkynyl, substituted alkynyl, amino-alkyl, substituted amino-alkyl, amino-alkoxy, substituted amino-alkoxy, amino-aryl, substituted amino-aryl, amino-aryloxy, substituted amino-aryloxy, wherein within R1-R12, or/and within R13-R16 or/and within R17-R20, respectively, two adjacent Rs can form an aromatic ring or a substituted aromatic ring, wherein the substituent is selected from hydrogen, alkyl, substituted alkyl, halide, cyano- or nitro-group, a hydrophilic group, like amino, substituted amino, alkylamino, substituted alkylamino, alkylammonium, substituted alkylammonium, carboxy, carboxylate, carboxylic acid ester, carbamoyl, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl, sulfoxide, phosphono, hydroxyphosphinoyl, hydroxyl-alkyl-phosphinoyl, phosphonate, phosphinate or, wherein within R1-R12, or/and within R13-R16, or/and within R17-R20, respectively, two adjacent Rs can form an aliphatic ring or a substituted aliphatic ring, wherein the substituent is selected from hydrogen, alkyl, substituted alkyl, halide, cyano- or nitro-group, a hydrophilic group, like amino, substituted amino, alkylamino, substituted alkylamino, alkylammonium, substituted alkylammonium, carboxy, carboxylate, carboxylic acid ester, carbamoyl, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl, sulfoxide, phosphono, hydroxyphosphinoyl, hydroxyl-alkyl-phosphinoyl, phosphonate, phosphinate, wherein, if in any of R1-R21 a substitution is present, the substituent in R1-R21 is each independently selected from a halide, cyano- or nitro-group, a hydrophilic group, like an amino, alkylamino, alkylammonium, carboxy, carboxylate, carboxylic acid ester, carbamoyl, hydroxy, alkyloxy, arylalkyloxy, aryloxy, alkylaryloxy, polyethylenoxy, polypropylenoxy, sulfanyl, alkylsulfonyl, arylsulfonyl, sulfo, sulfino, sulfeno, sulfonate, sulfinate, sulfenate, sulfamoyl, sulfoxide, phosphono, hydroxyphosphinoyl, hydroxyl-alkyl-phosphinoyl, phosphonate, phosphinate, wherein alkyl as used herein is a linear or branched alkyl chain with a length of 1-20 carbon atoms or a heteroalkyl chain with the length of 1-20 atoms comprising 1-4 heteroatoms selected from O, N, P, and S, wherein aryl is a 5, 6, or 7 member aryl ring system, or a 5, 6, or 7 member heteroaryl ring system comprising 1-3 heteroatoms selected from O, S and N, wherein at least one of R13-R20 is -Q-Z, wherein Q is a linker or a covalent bond, and wherein Z is a functional group and, wherein at least one of X and Y is N and the other X or Y independently is N or C.

The present invention also discloses a conjugate comprising the above compound and covalently bound thereto an affinity binding agent.

The present invention further relates to the use of a compound or of a conjugate as disclosed in the present invention for performing a luminescence measurement or an electrochemiluminescence reaction in an aqueous solution, especially, in an electrochemiluminescent device or electrochemiluminescent detection system.

Further, the present invention discloses a method for measuring an analyte by an in vitro method, the method comprising the steps of (a) providing a sample suspected or known to comprise the analyte, (b) contacting said sample with a conjugate according to the present invention under conditions appropriate for formation of an analyte conjugate complex, and (c) measuring the complex formed in step (b) and thereby obtaining a measure of the analyte.

DETAILED DESCRIPTION OF THE INVENTION

As indicated above, there is a need for novel metal-based chemiluminescent compounds, which are suitable for use in in vitro diagnostic assays.
Novel iridium-based chemiluminescent compounds of Formula I
The present invention relates to an iridium-based chemiluminescent compound of Formula I

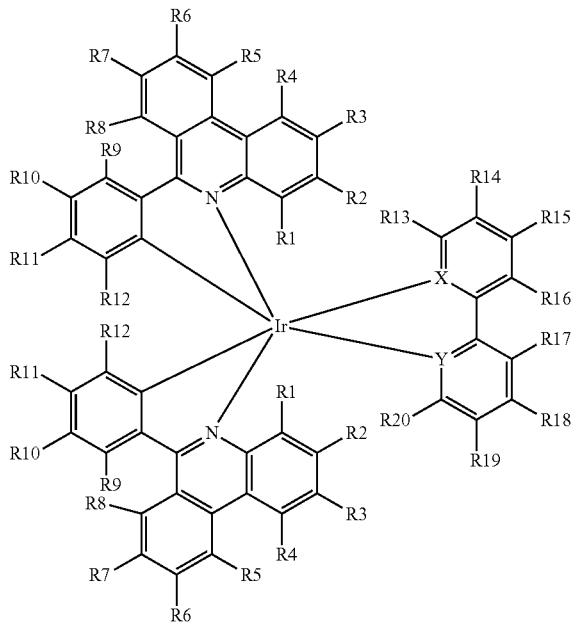

wherein each R1-R20 independently is hydrogen, halide, cyano- or nitro-group, amino, substituted amino, alkylamino, substituted alkylamino, arylamino, substituted arylamino, alkylammonium, substituted alkylammonium, carboxy, carboxylate, carboxylic acid ester, carbamoyl, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl, sulfoxide, phosphono, hydroxyphosphinoyl, hydroxy-alkyl-phosphinoyl, phosphonate, phosphinate or R21, wherein R21 is aryl, substituted aryl, alkyl, substituted alkyl, branched alkyl, substituted branched alkyl, arylalkyl, substituted arylalkyl, alkylaryl, substituted alkylaryl, alkenyl, substituted alkenyl, alkynyl, substituted alkynyl, amino-alkyl, substituted amino-alkyl, amino-alkoxy, substituted amino-alkoxy, amino-aryl, substituted amino-aryl, amino-aryloxy, substituted amino-aryloxy,
wherein within R1-R12, or/and within R13-R16 or/and within R17-R20, respectively, two adjacent Rs can form an aromatic ring or a substituted aromatic ring, wherein the substituent is selected from hydrogen, alkyl, substituted alkyl, halide, cyano- or nitro-group, a hydrophilic group, like amino, substituted amino, alkylamino, substituted alkylamino, alkylammonium, substituted alkylammonium, carboxy, carboxylate, carboxylic acid ester, carbamoyl, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl, sulfoxide, phosphono, hydroxyphosphinoyl, hydroxyl-alkyl-phosphinoyl, phosphonate, phosphinate or,
wherein within R1-R12, or/and within R13-R16, or/and within R17-R20, respectively, two adjacent Rs can form an aliphatic ring or a substituted aliphatic ring, wherein the substituent is selected from hydrogen, alkyl, substituted alkyl, halide, cyano- or nitro-group, a hydrophilic group, like amino, substituted amino, alkylamino, substituted alkylamino, alkylammonium, substituted alkylammonium, carboxy, carboxylate, carboxylic acid ester, carbamoyl, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl, sulfoxide, phosphono, hydroxyphosphinoyl, hydroxyl-alkyl-phosphinoyl, phosphonate, phosphinate,
wherein, if in any of R1-R21 a substitution is present, the substituent in R1-R21 is each independently selected from a halide, cyano- or nitro-group, a hydrophilic group, like an amino, alkylamino, alkylammonium, carboxy, carboxylate, carboxylic acid ester, carbamoyl, hydroxy, alkyloxy, arylalkyloxy, aryloxy, alkylaryloxy, polyethylenoxy, polypropylenoxy, sulfanyl, alkylsulfonyl, arylsulfonyl, sulfo, sulfino, sulfeno, sulfonate, sulfinate, sulfenate, sulfamoyl, sulfoxide, phosphono, hydroxyphosphinoyl, hydroxyl-alkyl-phosphinoyl, phosphonate, phosphinate,
wherein alkyl as used herein is a linear or branched alkyl chain with a length of 1-20 carbon atoms or a heteroalkyl chain with the length of 1-20 atoms comprising 1-4 heteroatoms selected from O, N, P, and S, wherein aryl is a 5, 6, or 7 member aryl ring system, or a 5, 6, or 7 member heteroaryl ring system comprising 1-3 heteroatoms selected from O, S and N,
wherein at least one of R13-R20 is -Q-Z, wherein Q is a linker or a covalent bond, and wherein Z is a functional group and, wherein at least one of X and Y is N and the other X or Y independently is N or C.

A compound of Formula I comprises two ligands derived from phenylphenanthridine as defined via the definitions given for Formula I and one third ligand.

In one embodiment one of R13 to R20 of Formula I is -Q-Z.

As known to a person skilled in the art, the substituents in R1-R21 can be further substituted, for example, an alkyl-group in an aminoalkyl-group can be further substituted by a hydroxyl, amino, carboxy, or sulfo group.

As used herein, including the accompanying claims, the substituents have the meanings commonly known to the skilled person.

Alkyl, preferably, is a linear or branched alkyl chain with a length of 1-20 carbon atoms, preferably with a length of 1-10 carbon atom, particular preferred with a length of 1-6 carbon atoms; or a heteroalkyl chain with the length of 1-20 atoms, preferably with a length of 1-10 carbon atom, comprising 1-4 heteroatoms selected from O, N, P, and S. Examples of alkyl groups include, but are not limited to, methyl, ethyl, propyl, isopropyl, butyl, isobutyl, tert.-butyl, the isomeric pentyls, the isomeric hexyls, the isomeric heptyls, the isomeric octyls, and dodecyl. In a particular preferred embodiment, alkyl is methyl or ethyl.

The terms alkoxy and alkyloxy as well as substituted alkyl and substituted alkoxy, respectively, may be used interchangeably. Alkoxy and alkyloxy mean a moiety of the formula —OR, wherein R preferably is an alkyl moiety as defined hereinabove. Examples of alkoxy moieties include, but are not limited to, methoxy, ethoxy, and isopropoxy.

In one embodiment preferred substituents for substituted alkyloxy are ethylenoxy chains comprising 1-40 ethylenoxy units, or comprising 1-20 ethylenoxy units or comprising 1-10 ethylenoxy units.

Aryl, preferably, is a 5, 6, or 7 member aryl ring system, preferably a 6 member aryl ring system, or a 5, 6, or 7 member heteroaryl ring system comprising 1-3 heteroatoms selected from O, S and N, preferably a 6 member heteroaryl ring system. In a particular preferred embodiment, aryl is phenyl.

In one embodiment, in Formula I each $R_1$-$R_{20}$ independently is hydrogen, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl or sulfoxide.

In one embodiment, in Formula I each $R_1$-$R_{20}$ independently is hydrogen, substituted or unsubstituted alkyloxy, substituted or unsubstituted aryloxy, substituted or unsubstituted alkylsulfonyl, substituted or unsubstituted arylsulfonyl, sulfonate, sulfinate, sulfenate, sulfamoyl or sulfoxide.

In one embodiment, in Formula I each $R_1$-$R_{20}$ independently is hydrogen, substituted or unsubstituted alkyloxy, substituted or unsubstituted alkylsulfonyl, substituted or unsubstituted arylsulfonyl, sulfonate or sulfoxide.

In one embodiment at least one of R1 to R20 of the compound according to Formula I is substituted by at least one hydrophilic group.

In one embodiment at least one of R1 to R12 of the phenylphenanthridine residues comprised in Formula I, Formula I (a) and/or Formula I (b) of Formula II as defined herein, respectively, is substituted by at least one hydrophilic group, in particular by at least one hydrophilic group as defined below.

Preferred hydrophilic groups are amino, alkylamino, with alkyl meaning a linear chain such as methyl, ethyl, propyl, butyl, pentyl chain or a branched alkyl chain such as isopropyl, isobutyl, tert. butyl, preferably a linear alkyl chain such as methyl or ethyl, substituted alkylamino, this contains for example one or two branched or linear chains bound to the N-atom, which are substituted by an additional hydrophilic group such as hydroxyl or sulfo, preferably this substituted alkylamino contains two hydroxypropyl or hydroxyethyl residues, arylamino, with aryl referring to an aromatic residue, such as phenyl, or naphthyl, preferably phenyl, substituted arylamino, with aryl as defined above and an additional residue formed by a hydrophilic group, alkylammonium, with alkyl as defined above and preferably being a trimethylammonium residue or triethylammonium residue, substituted alkylammonium, carboxy, carboxylic acid ester, preferably an alkyl ester such as methyl or ethyl ester, carbamoyl, hydroxy, substituted or unsubstituted alkyloxy with alkyl and substituted alkyl being as defined above or aryloxy or substituted aryloxy with aryl and substituted aryl being as defined above, sulfanyl, substituted or unsubstituted alkylsulfonyl, substituted or unsubstituted arylsulfonyl, sulfo, sulfino, sulfeno, sulfamoyl, sulfoxide, phosphono, hydroxyphosphinoyl, hydroxy-alkyl-phosphinoyl, phosphonate, phosphinate.

Preferably such hydrophilic group is selected from amino, alkylamino, substituted alkylamino, arylamino, substituted arylamino, alkylammonium, substituted alkylammonium, carboxy, hydroxy, sulfo, sulfeno, sulfamoyl, sulfoxide and phosphonate, where applicable, each preferably as defined in the above paragraph.

In a preferred embodiment, the hydrophilic group is selected from alkylamino, alkylammonium, substituted alkylammonium, carboxy, hydroxy, sulfo, sulfeno, sulfamoyl, sulfoxide and phosphonate.

In a further particular preferred embodiment the hydrophilic group is selected from a sulfo group and a sulfamoyl group.

In one embodiment at least one of R1-R12 is a substituted or unsubstituted group selected from sulfo-alkyl, sulfo-aryl, sulfo-alkoxy, sulfo-aryloxy, sulfo, sulfino-alkyl, sulfino-aryl, sulfino-alkoxy, sulfino-aryloxy, sulfino, sulfeno-alkyl, sulfeno-aryl, sulfeno-alkoxy, sulfeno-aryloxy, sulfeno, sulfamoyl-alkyl, sulfamoyl-aryl, sulfamoyl-alkoxy, sulfamoyl-aryloxy, sulfamoyl, alkanesulfonyl-alkyl, alkanesulfonyl-aryl, alkanesulfonyl, arenesulfonyl-alkyl, or arenesulfonyl-aryl, or arenesulfonyl, sulfoamino-alkyl, sulfoamino-aryl, sulfoamino-alkoxy, sulfoamino-aryloxy, sulfoamino, sulfinoamino-alkyl, sulfinoamino-aryl, sulfinoamino-alkoxy, sulfinoamino-aryloxy, sulfinoamino, alkanesulfonylamino-alkyl, alkanesulfonylamino-aryl, alkanesulfonylamino-alkoxy, alkanesulfonylamino-aryloxy, alkanesulfonylamino, arenesulfonylamino-alkyl, arenesulfonylamino-aryl, arenesulfonylamino-alkoxy, arenesulfonylamino-aryloxy, arenesulfonylamino, alkanesulfinylamino-alkyl, alkanesulfinylamino-aryl, alkanesulfinylamino-alkoxy, alkanesulfinylamino-aryloxy, alkanesulfinylamino, arenesulfinylamino-alkyl, arenesulfinylamino-aryl, arenesulfinylamino-alkoxy, arenesulfinylamino-aryloxy, arenesulfinylamino, phosphono-alkyl, phosphono-aryl, phosphono-alkyloxy, phosphono-aryloxy, phosphono, hydroxyphosphinoyl-alkyl, hydroxyphosphinoyl-aryl, hydroxyphosphinoyl-alkyloxy, hydroxyphosphinoyl-aryloxy, hydroxyphosphinoyl, hydroxy-alkyl-phosphinoyl-alkyl, hydroxy-alkyl-phosphinoyl-aryl, hydroxy-alkyl-phosphinoyl-alkyloxy, hydroxy-alkyl-phosphinoyl-aryloxy, hydroxy-alkyl-phosphinoyl, phosphonoamino-alkyl, phosphonoamino-aryl, phosphonoamino-alkoxy, phosphonoamino-aryloxy, phosphonoamino, or, where chemically matching, a salt of the above described substituents, wherein alkyl is a linear or branched alkyl chain with a length of 1-20 carbon atoms or a heteroalkyl chain with the length of 1-20 atoms comprising 1-4 heteroatoms selected from O, N, P, and S and wherein aryl as used herein is a 5, 6, or 7 member aryl ring system, or a 5, 6, or 7 member heteroaryl ring system comprising 1-3 heteroatoms selected from O, S and N.

In one embodiment at least one of R1 to R12 is a substituted or unsubstituted group selected from sulfo-alkyl, sulfo-aryl, sulfo-alkoxy, sulfo-aryloxy, sulfo, sulfamoyl-alkyl, sulfamoyl-aryl, sulfamoyl-alkoxy, sulfamoyl-aryloxy, sulfamoyl, alkanesulfonyl-alkyl, alkanesulfonyl-aryl, alkanesulfonyl, arenesulfonyl-alkyl, arenesulfonyl-aryl, arenesulfonyl, alkanesulfonylamino-alkyl, alkanesulfonylamino-aryl, alkanesulfonylamino-alkoxy, alkanesulfonylamino-aryloxy, alkanesulfonylamino, arenesulfonylamino-alkyl, arenesulfonylamino-aryl, arenesulfonylamino-alkoxy, arenesulfonylamino-aryloxy, arenesulfonylamino, phosphono-alkyl, phosphono-aryl, phosphono-alkyloxy, phosphono-aryloxy, phosphono, hydroxyphosphinoyl-alkyl, hydroxyphosphinoyl-aryl, hydroxyphosphinoyl-alkyloxy, hydroxyphosphinoyl-aryloxy, hydroxyphosphinoyl, hydroxy-alkyl-phosphinoyl-alkyl, hydroxy-alkyl-phosphinoyl-aryl, hydroxy-alkyl-phosphinoyl-alkyloxy, hydroxy-alkyl-phosphinoyl-aryloxy, hydroxy-alkyl-phosphinoyl, or, where chemically matching, a salt of the above described substituents, wherein alkyl is a linear or branched alkyl chain with a length of 1-20 carbon atoms or a heteroalkyl chain with the length of 1-20 atoms comprising 1-4 heteroatoms selected from O, N, P, and S and wherein aryl as used herein is a 5, 6, or 7 member aryl ring system, or a 5, 6, or 7 member heteroaryl ring system comprising 1-3 heteroatoms selected from O, S and N.

In one embodiment at least one of R1 to R12 is sulfo-alkyl, sulfo-aryl, sulfo-alkoxy, sulfo-aryloxy, sulfo, or a salt thereof (=sulfonate), wherein the counter ion is preferably a cation from the group of alkali metals.

In one embodiment at least one of R1 to R12 is sulfo-alkyl, sulfo-alkoxy, sulfo, or a salt thereof (=sulfonate), wherein the counter ion is a cation from the group of alkali metals.

In one embodiment at least one of R1 to R12 is sulfo-methyl, sulfo-alkoxy with a C2 to C4 alkyl chain, or a salt thereof (=sulfonate) wherein the counter ion is a cation from the group of alkali metals.

In one embodiment at least one of the groups R1 to R12 of Formula I is a sulfo group.

In one embodiment, one to three of R1 to R12 are not hydrogen.

In one embodiment, the counter ion is an alkali metal cation selected from the group consisting of lithium cation, sodium cation, potassium cation and caesium cation.

In one embodiment, the counter ion is an alkali metal cation selected from the group consisting of sodium cation and caesium cation.

In one embodiment, the counter ion is a caesium cation.

In one embodiment the phenylphenanthridine residues comprised in Formula I are selected from the below given substituted phenylphenanthridines.

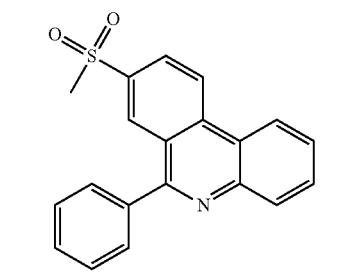

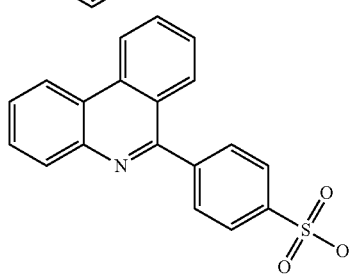

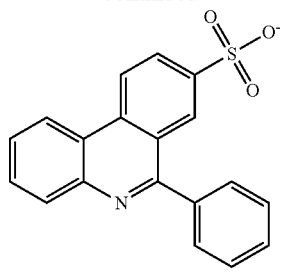

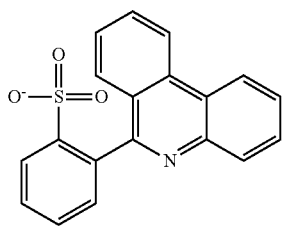

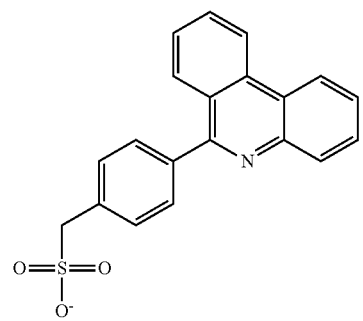

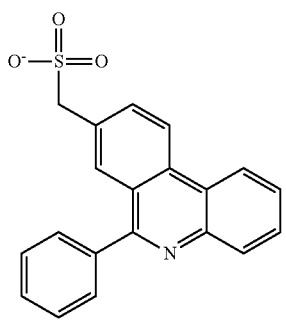

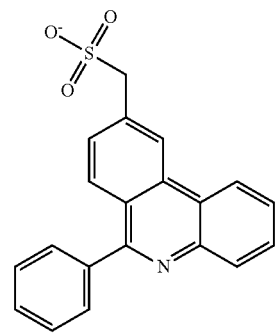

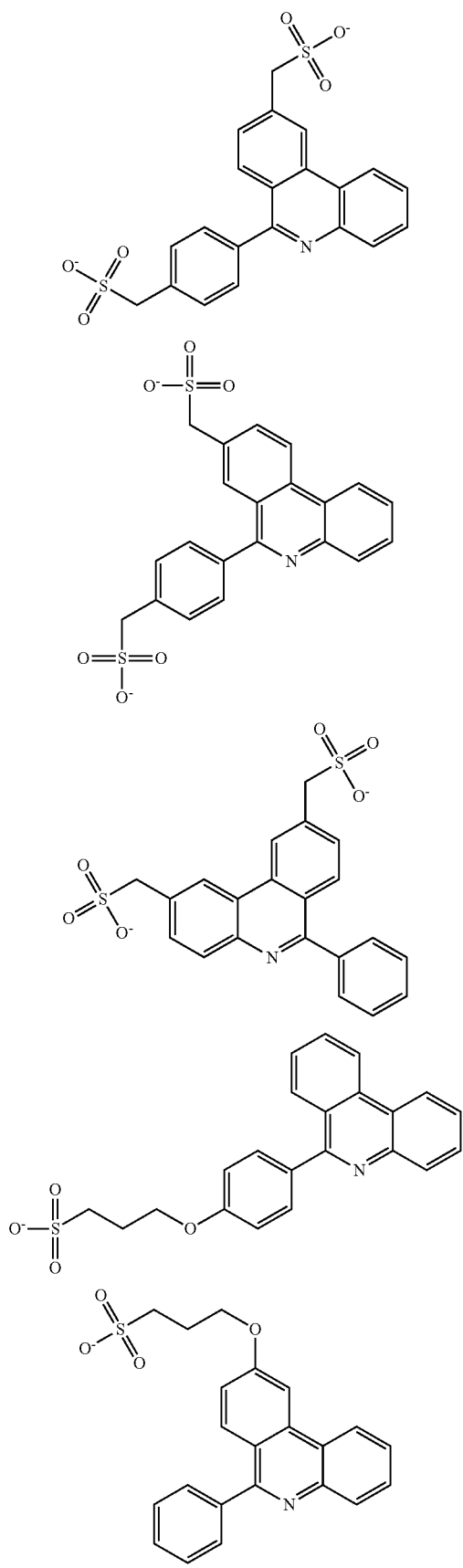

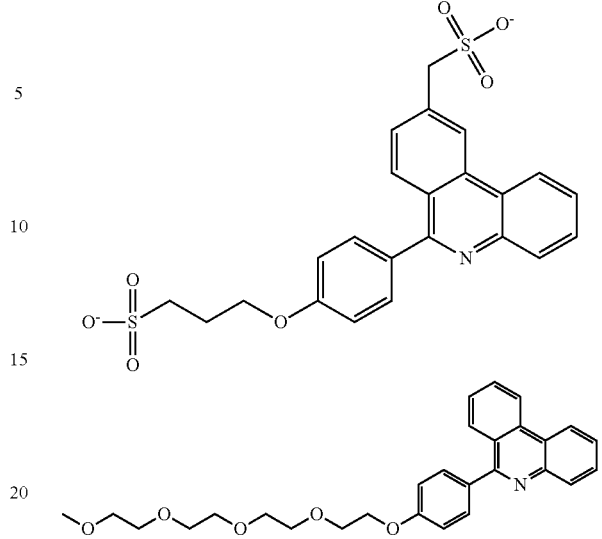

The term "linker" as used herein, has the meaning known to a person skilled in the art and relates to a molecule or groups of molecules, which are used to link fragments of molecules. Linkers are characterized by having two or more chemically orthogonal functionalities on a flexible or rigid scaffold. A covalent bond is not a linker in the sense of the present invention.

In the compound according to the present invention Q either is a covalent bond or a linker having a backbone length of between 1 and 200 atoms. With other words if the backbone length is between 1 and 200 atoms, the shortest connection between an aromatic ring of the third ligand of Formula I and the functional group Z consists of 1 to 200 atoms.

In case a ring system is present the shortest number of atoms in the ring system is taken when assessing the linker length. As an example, a phenylene ring accounts for a length of four atoms in a linker.

In one embodiment Q is a covalent bond or a linker having as a backbone a straight or branched saturated, unsaturated, unsubstituted or substituted C1-C200 alkyl chain, or a 1 to 200 atom chain consisting of carbon atoms, substituted carbon atoms and/or one or more atoms selected from O, N, P and S, or substituted N, P, S atoms, or a chain as described before with the backbone containing one or more cyclic or heterocyclic aromatic or non-aromatic ring systems.

In one embodiment Q is a covalent bond or is a linker and has as a backbone a straight or branched saturated, unsaturated, unsubstituted or substituted C1-C100 alkyl chain, or a 1 to 100 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

In one embodiment Q is a covalent bond or is a linker and has as a backbone a straight or branched saturated, unsaturated, unsubstituted or substituted C1-C50 alkyl chain, or a 1 to 50 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

In one further embodiment Q is a covalent bond or is a linker and has as backbone a straight or branched saturated, unsaturated, unsubstituted or substituted C1-C20 alkyl chain, or a 1 to 20 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

In one embodiment, Q, for example the linker Q, in the electrochemiluminescent complex of this invention is a straight or branched saturated, unsaturated, unsubstituted, substituted C1-C20 alkyl chain, or a C1-C20 arylalkyl chain (wherein e.g. a phenylene ring accounts for a length of four carbon atoms), or a 1 to 20 atom chain with a backbone consisting of carbon atoms, substituted carbon atoms and/or one or more atoms selected from O, N, P and S, or substituted N, P, or S atoms, or a 1 to 20 atom chain, or with a backbone consisting of carbon atoms, substituted carbon atoms and one or more atoms selected from O, N, P and S, or substituted N, P, or S atoms comprising at least one aryl, heteroaryl, substituted aryl or substituted heteroaryl group (wherein e.g. a phenylene ring accounts for a length of four atoms).

In one embodiment Q, for example the linker Q in a compound according to the present invention is a saturated C1-C12 alkyl chain, or a C1-C12 arylalkyl chain, or a 1 to 12 atom chain with a backbone consisting of carbon atoms, substituted carbon atoms and one or more atoms selected from O, N, P and S, or substituted N, P, or S atoms, or a 1 to 12 atom chain with a backbone consisting of carbon atoms, substituted carbon atoms and one or more atoms selected from O, N, P and S, or substituted N, P, or S atoms comprising at least one aryl, heteroaryl, substituted aryl or substituted heteroaryl group (wherein e.g. a phenylene ring accounts for a length of four atoms).

In one embodiment Q is a covalent bond. In case Q is a covalent bond the functional group Z is at least one of R13 to R20. In one embodiment one of R13 to R20 is Z.

In one embodiment Q-Z is maleimide.

In one embodiment the linker Q comprises one or more amino acid(s).

In one embodiment the linker Q comprises one or more nucleotide(s).

In one embodiment both X and Y in Formula I are N.

In one embodiment the functional group Z comprised in the iridium-based complex of Formula I according to the present invention is selected from the group consisting of aldehyde, carboxylic acid, carboxylic acid ester, epoxide, N-hydroxysuccinimide ester, amino group, halogen, hydrazine, hydroxyl, sulfhydryl, maleimido, alkynyl, azide, isocyanate, isothiocyanate and phosphoramidite.

In one embodiment the functional group Z comprised in the iridium-based complex of Formula I according to the present invention is selected from the group consisting of carboxylic acid, N-hydroxysuccinimide ester, amino group, halogen, sulfhydryl, maleimido, alkynyl, azide, isocyanate, isothiocyanate, and phosphoramidite.

In a particular preferred embodiment, the functional group Z comprised in the iridium-based complex of Formula I according to the present invention is selected from the group consisting of carbocyclic acid, N-hydroxysuccinimide ester and maleimido.

In a particular preferred embodiment, the functional group Z comprised in the iridium-based complex of Formula I according to the present invention is selected from the group consisting of N-hydroxysuccinimide ester and maleimido.

In one embodiment, the present invention relates to a compound of Formula I,
wherein one to three of R1 to R12 of the phenylphenanthridine residues are independently sulfo-alkyl, sulfo-aryl, sulfo-alkoxy, sulfo-aryloxy, sulfo, or a salt thereof (=sulfonate),
wherein the counter ion is preferably a cation from the group of alkali metals, and the other groups R1 to R12 are hydrogen, wherein one of R13-R20 is -Q-Z, wherein Q is a linker or a covalent bond, and wherein Z is a functional group and the other groups R13 to R20 in Formula I are hydrogen or R21, wherein R21 is alkyl, and wherein X and Y are N.

In one embodiment, the present invention relates to a compound of Formula I, wherein the phenylphenanthridine residues comprised in Formula I are selected from the below given substituted phenylphenanthridines

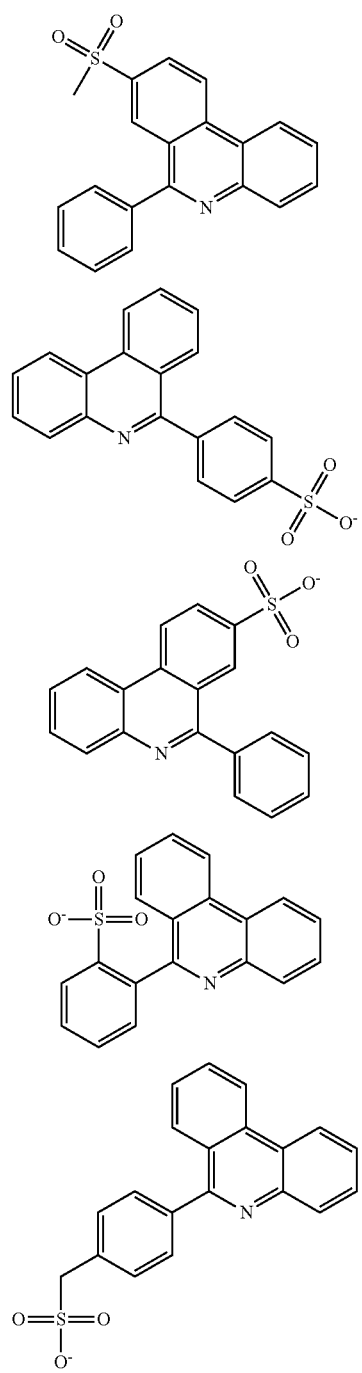

-continued

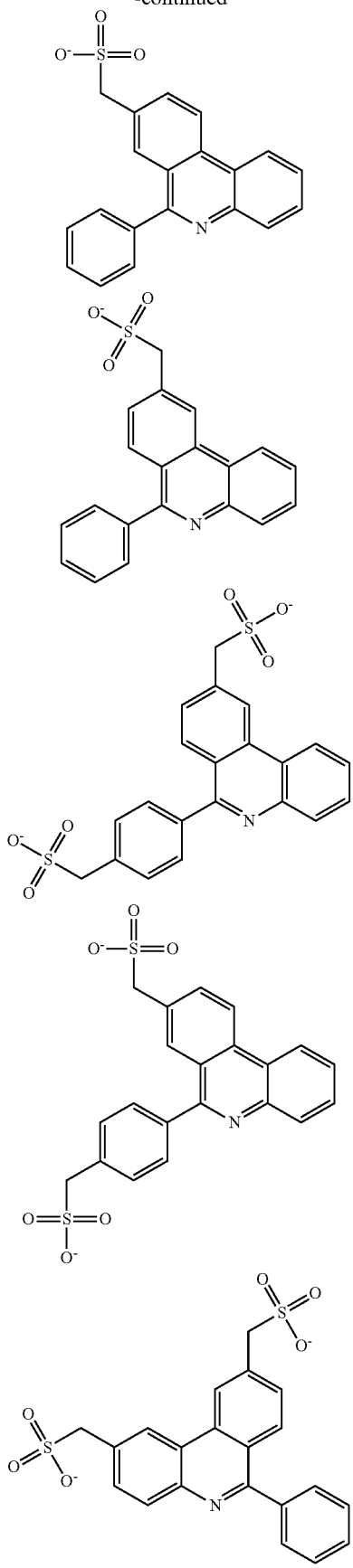

-continued

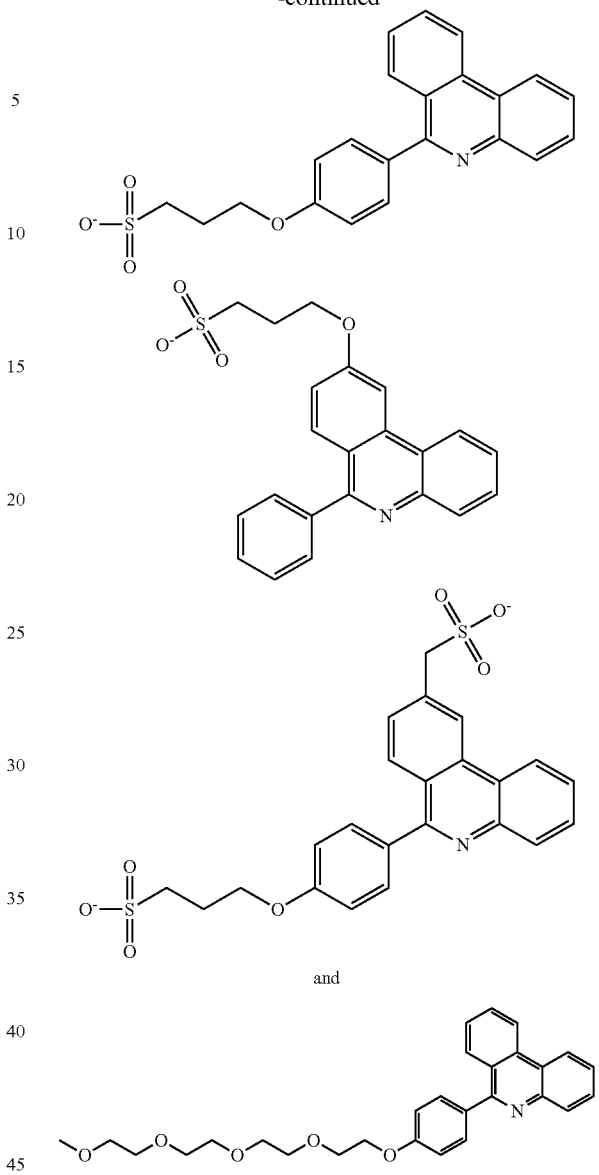

wherein one of R13-R20 is -Q-Z, wherein Q is a linker or a covalent bond, and wherein Z is a functional group and the other groups R13 to R20 in Formula I are hydrogen or R21, wherein R21 is alkyl, and
wherein X and Y are N.

In one embodiment, the present invention relates to a compound of Formula I,
wherein R1 to R12 are hydrogen,
wherein one of R13-R20 is -Q-Z, wherein Q is a linker or a covalent bond, and wherein Z is a functional group, preferably carboxylic acid, and the other groups R13 to R20 in Formula I are hydrogen or R21, wherein R21 is alkyl, and
wherein X and Y are N.

Any combinations of any embodiments of the compounds of Formula I as defined above are considered to be within the scope of the invention.

It has now been surprisingly and unexpectedly found that the iridium-based chemiluminescent compounds of Formula I are suitable as labels for future high sensitive ECL-based detection methods.

Novel Iridium-Based Chemiluminescent Compounds of Formula II

In one embodiment the present invention relates to a compound according to Formula II

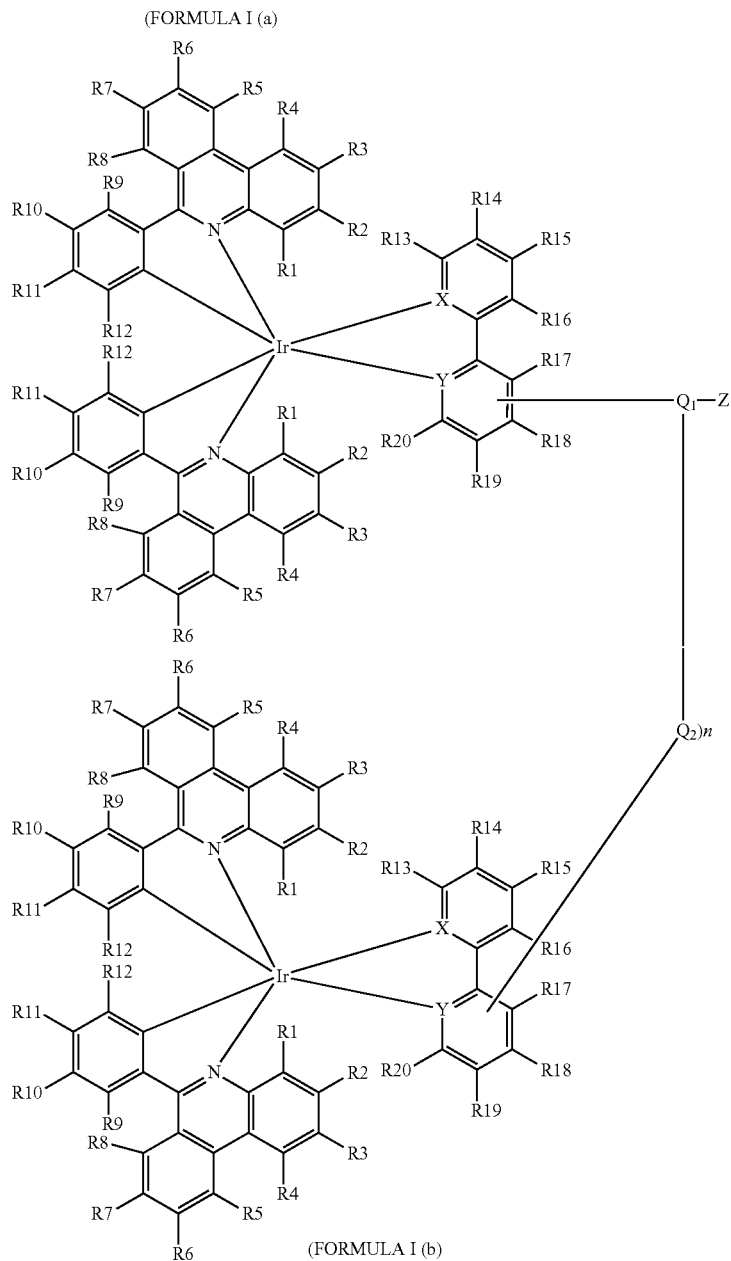

wherein in Formula I (a) and in Formula I (b), respectively and independently, R1 to R20 are as defined for Formula I, with the exception that Q of Formula I is Q1 or Q2 in Formula II, respectively, wherein Q1 is a linker, preferably wherein at least one of R13-R20 in Formula I (a) is -Q1-Z and wherein Q1 is a linker;

wherein at least one of R13-R20 in Formula I (b) is Q2 and each Q2 independently is a linker or a covalent bond, wherein (n) is an integer from 1 to 50, wherein X and Y are as defined for Formula I, and wherein Z is a functional group.

In one embodiment one of R13 to R20 of Formula I (a) in Formula II is Q1-Z.

In one embodiment one of R13 to R20 in each of Formula I (b) in Formula II is Q2.

In one embodiment one of R13 to R20 of Formula I (a) in Formula II is Q1-Z and one of R13 to R20 in each of Formula I (b) in Formula II is Q2.

A compound of Formula I (a) and Formula I (b), respectively, comprises two ligands derived from phenylphenanthridine as defined via the definitions given above for Formula I and one third ligand.

In one embodiment, R1 to R20 have the same meanings as described above for R1 to R20 for the compounds of Formula II.

In one embodiment Formula I (a) and Formula I (b) are the same, except for Q1-Z in Formula I (a) and Q2 in Formula I (b), respectively.

As the skilled person will readily appreciate the linker Q1 of Formula II comprises n branching sites at which Q2 is bound.

In one embodiment Q1 of Formula II has as a backbone a straight or branched saturated, unsaturated, unsubstituted or substituted C1-C200 alkyl chain, or a 1 to 200 atom chain consisting of carbon atoms, substituted carbon atoms and/or one or more atoms selected from O, N, P and S, or substituted N, P, S atoms, or a chain as described before with the backbone containing one or more cyclic or heterocyclic aromatic or non-aromatic ring systems.

In one embodiment the linker Q1 of Formula II has as a backbone a straight or branched saturated, unsaturated, unsubstituted or substituted C1-C100 alkyl chain, or a 1 to 100 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

In one embodiment the linker Q1 of Formula II has as a backbone a straight or branched saturated, unsaturated, unsubstituted or substituted C1-C50 alkyl chain, or a 1 to 50 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

In one further embodiment the linker Q1 of Formula II has as a backbone a straight or branched saturated, unsaturated, unsubstituted or substituted C1-C20 alkyl chain, or a 1 to 20 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

In one embodiment, the linker Q1 of Formula II in the electrochemiluminescent complex of this invention is a straight or branched saturated, unsaturated, unsubstituted, substituted C1-C20 alkyl chain, or a C1-C20 arylalkyl chain (wherein e.g. a phenylene ring accounts for a length of four carbon atoms), or a 1 to 20 atom chain with a backbone consisting of carbon atoms, substituted carbon atoms and/or one or more atoms selected from O, N, P and S, or substituted N, P, or S atoms, or a 1 to 20 atom chain, or with a backbone consisting of carbon atoms, substituted carbon atoms and one or more atoms selected from O, N, P and S, or substituted N, P, or S atoms, comprising at least one aryl, heteroaryl, substituted aryl or substituted heteroaryl group (wherein e.g. a phenylene ring accounts for a length of four atoms).

In one embodiment Q1, for example the linker Q1, in a compound according to the present invention is a saturated C1-C12 alkyl chain, or a C1-C12 arylalkyl chain, or a 1 to 12 atom chain with a backbone consisting of carbon atoms, substituted carbon atoms and one or more atoms selected from O, N, P and S, or substituted N, P, or S atoms, or a 1 to 12 atom chain with a backbone consisting of carbon atoms, substituted carbon atoms and one or more atoms selected from O, N, P and S, or substituted N, P, or S atoms, comprising at least one aryl, heteroaryl, substituted aryl or substituted heteroaryl group (wherein e.g. a phenylene ring accounts for a length of four atoms).

Formula I (b) and Q2 are present (n) times in a compound according to Formula II with (n) being an integer of 1-50. Each of these (n) Q2s independently is a covalent bond or a linker having as a backbone a straight or branched saturated, unsaturated, unsubstituted or substituted C1-C200 alkyl chain, or a 1 to 200 atom chain consisting of carbon atoms, substituted carbon atoms and/or one or more atoms selected from O, N, P and S, or substituted N, P, S atoms, or a chain as described before with the backbone containing one or more cyclic or heterocyclic aromatic or non-aromatic ring systems.

In one embodiment each Q2 of Formula II independently is a covalent bond or a linker having as backbone a straight or branched saturated, unsaturated, unsubstituted or substituted C1-C100 alkyl chain, or a 1 to 100 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

In one embodiment each Q2 of Formula II independently is a covalent bond or a linker having as backbone a straight or branched saturated, unsaturated, unsubstituted or substituted C1-050 alkyl chain, or a 1 to 50 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

In one embodiment each Q2 of Formula II independently is a covalent bond or a linker having as backbone a straight or branched saturated, unsaturated, unsubstituted or substituted C1-C20 alkyl chain, or a 1 to 20 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

In one embodiment each Q2 of Formula II independently is a covalent bond or a linker having as a backbone a saturated C1-C12 alkyl chain or a 1 to 12 atom chain with a backbone consisting of carbon atoms, substituted carbon atoms and/or one or more atoms selected from O, N, P and S, or substituted N, P, or S atoms or a chain as described before with the backbone containing one or more cyclic or heterocyclic aromatic or non-aromatic ring systems.

In one embodiment the linker Q1 comprises one or more amino acid(s).

In one embodiment, the linker Q1 comprises a peptide chain.

In one embodiment the linker Q2 comprises one or more amino acid(s).

In one embodiment both the linkers Q1 and Q2 comprise one or more amino acid(s).

In one embodiment the linker Q1 comprises one or more nucleotide(s).

In one embodiment the linker Q2 comprises one or more nucleotide(s).

In one embodiment both the linkers Q1 and Q2 comprise one or more nucleotide(s).

In one embodiment, the linker Q2 is selected from the group consisting of —$C_6H_4$—$(CH_2)_2$— and —$C_6H_4$—$(CH_2)_2$—CO—.

In Formula II (n) is an integer of 1-50, indicating that Formula I (b) and Q2 are present (n) times in the compound according to Formula II. In certain embodiments (n) is an integer from 2 to 50, or from 1 to 40, or from 2 to 40, or from 3 to 31.

In Formula II (n) is an integer of 1-50, indicating that Formula I (b) and Q2 are present (n) times in the compound according to Formula II. In certain embodiments (n) is an integer from 1 to 49, from 1 to 48, from 1 to 47, from 1 to 46, from 1 to 45, from 1 to 44, from 1 to 43, from 1 to 42, from 1 to 41, from 1 to 40, from 2 to 50, from 2 to 49, from 2 to 48, from 2 to 47, from 2 to 46, from 2 to 45, from 2 to 44, from 2 to 43, from 2 to 42, from 2 to 41, from 2 to 40, from 3 to 39, from 3 to 38, from 3 to 37, from 3 to 36, from 3 to 35, from 3 to 34, from 3 to 33, from 3 to 32, from 3 to 31, from 3 to 30, from 4 to 29, from 4 to 28, from 4 to 27, from 4 to 26, from 4 to 25, from 4 to 24, from 4 to 23, from 4 to 22, from 4 to 21, from 4 to 20, from 5 to 19, from 5 to 18, from 5 to 17, from 5 to 16, from 5 to 15, from 5 to 14, from 5 to 13, from 5 to 12, from 5 to 11, or from 5 to 10.

In one embodiment, in Formula II, (n) is 1.
In one embodiment, in Formula II, (n) is 2.
In one embodiment, in Formula II, (n) is 3.

In one embodiment the functional group Z comprised in the iridium-based complex of Formula II according to the present invention is selected from the group consisting of aldehyde, carboxylic acid, carboxylic acid ester, epoxide, N-hydroxysuccinimide ester, amino group, halogen, hydrazine, hydroxyl, sulfhydryl, maleimido, alkynyl, azide, isocyanate, isothiocyanate and phosphoramidite.

In one embodiment the functional group Z comprised in the iridium-based complex of Formula II according to the present invention is selected from the group consisting of carboxylic acid, N-hydroxysuccinimide ester, amino group, halogen, sulfhydryl, maleimido, alkynyl, azide, isocyanate, isothiocyanate, and phosphoramidite.

In a particular preferred embodiment, the functional group Z comprised in the iridium-based complex of Formula II according to the present invention is selected from the group consisting of N-hydroxysuccinimide ester and maleimido.

Any combinations of any embodiments of the compounds of Formula II as defined above are considered to be within the scope of the invention.

It has now been surprisingly and unexpectedly found that the iridium-based chemiluminescent compounds of Formula II are suitable as labels for future high sensitive ECL-based detection methods.

Processes for the Preparation of Compounds of Formulae I and II

The invention, in one aspect, relates to novel processes for the preparation of compounds of Formula I and compounds of Formula II, respectively.

Compounds according to Formula I can e.g. be synthesized (based on Lamansky, S., Inorg. Chem. 40 (2001) 1704-1711) as follows: Synthesis of the substituted phenyl-phenanthridine dimer iridium complex; reacting this dimer with a precursor of Q-Z to give a product according to Formula I.

In accordance with this process the compounds of Formula I can be e.g. obtained as shown in Scheme 1 below.

Scheme 1: Synthesis of a compound of Formula I.

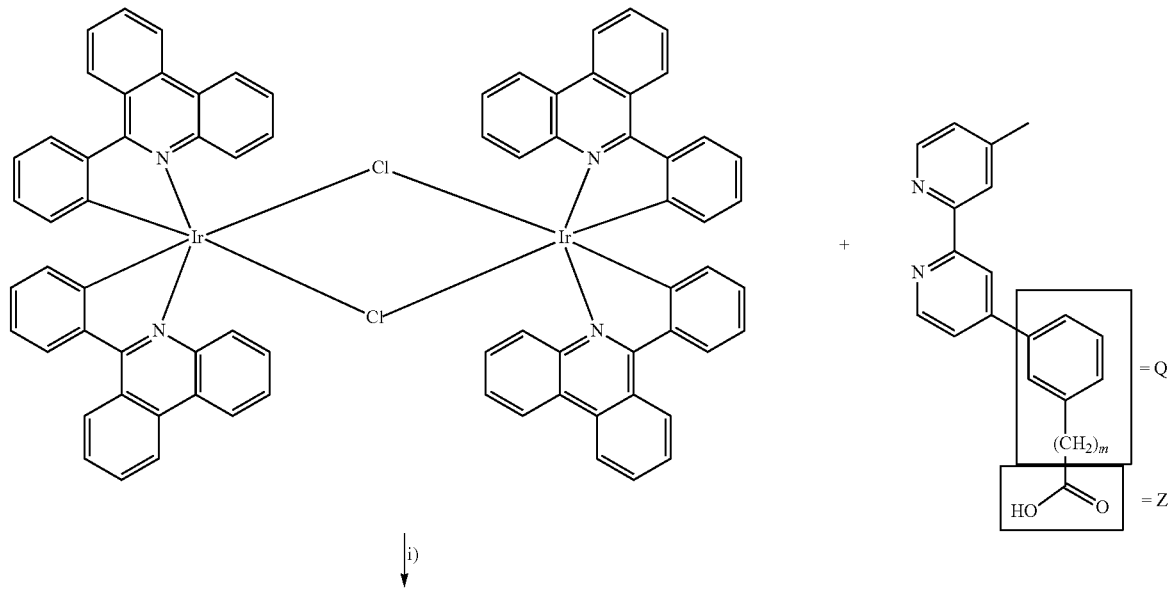

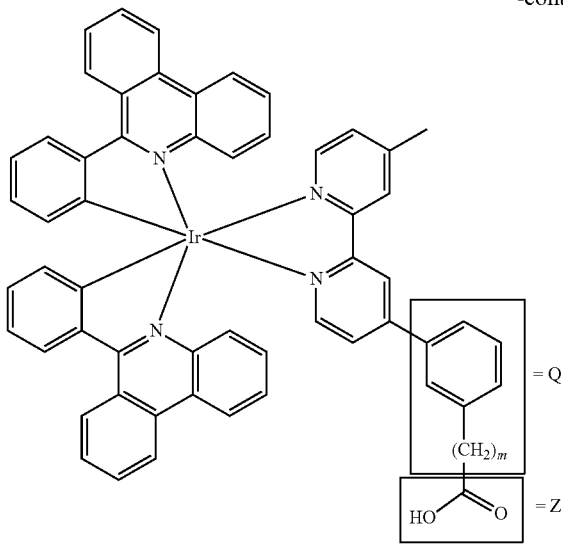

I

Reagents and conditions: (i): Na$_2$CO$_3$, 2-ethoxyethanol; m is an integer from 1 to 17.

The substituted phenyl-phenanthridine dimer iridium complex used as starting material can be obtained by a processes as e.g. shown in the Examples (cf. Example 2) and as described e.g. in EP 12179056.2.

Compounds according to Formula II can e.g. be synthesized (based on Lamansky, S., Inorg. Chem. 40 (2001) 1704-1711) as follows: Synthesis of the substituted phenyl-phenanthridine dimer iridium complex; reacting this dimer with a precursor of the linker Q which contains 1-50 third ligand moieties to give a product according to Formula II.

In accordance with this process the compounds of Formula II can be e.g. obtained as shown in Scheme 2 below.

Scheme 2: Synthesis of a compound of Formula II. Reagents and conditions: Cs$_2$CO$_3$, DMF

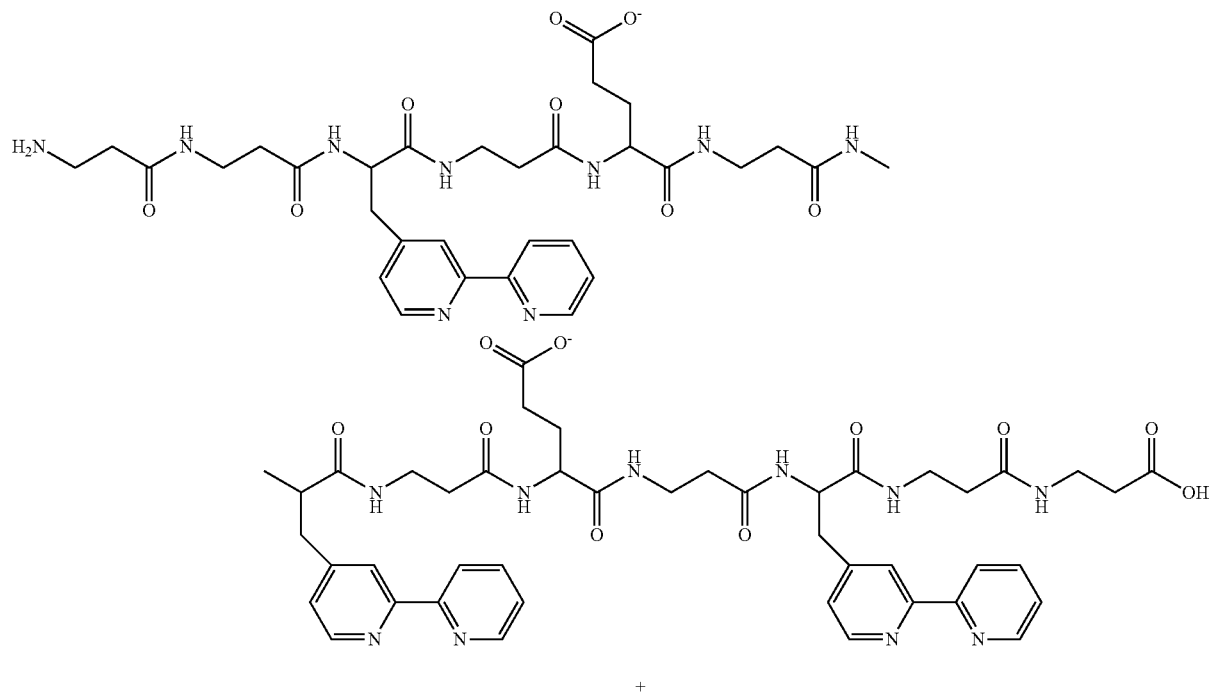

+

-continued
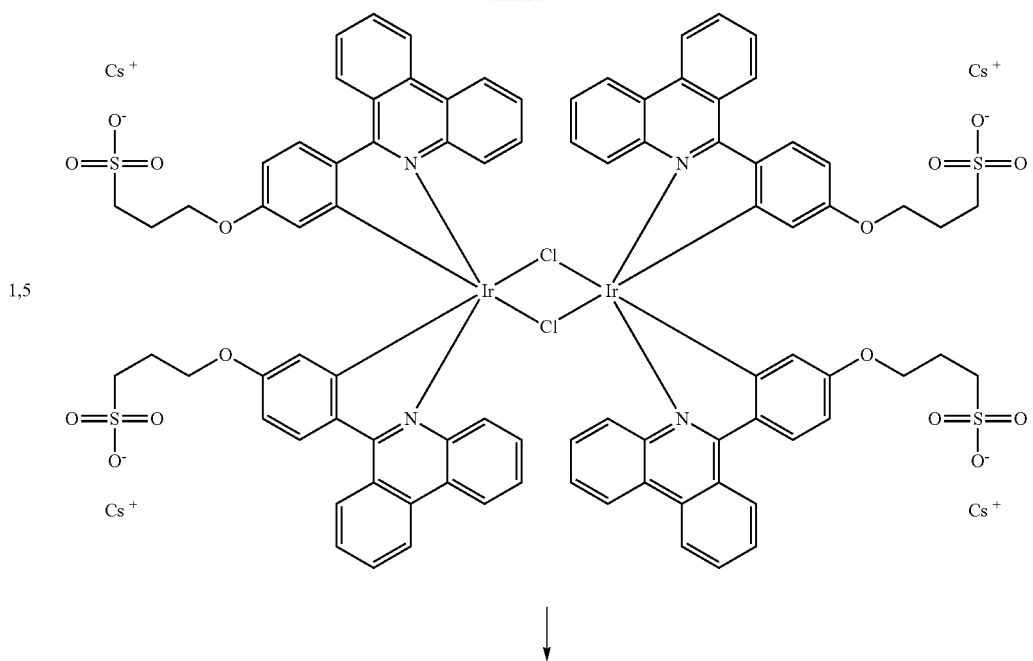
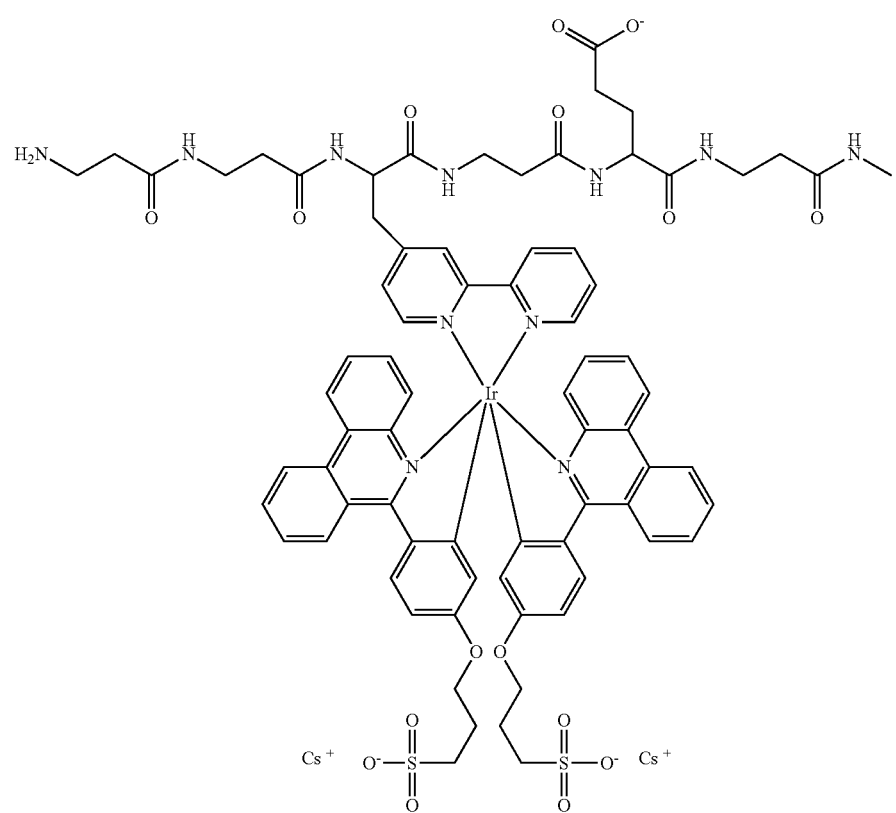

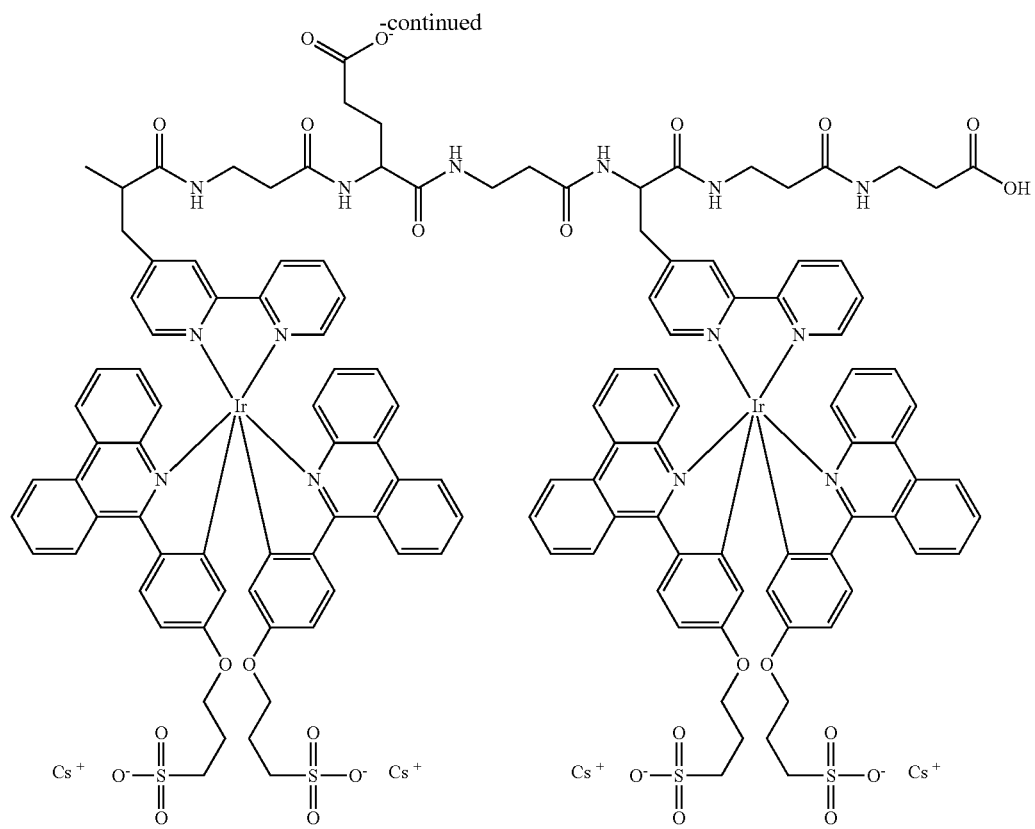

The substituted phenyl-phenanthridine dimer iridium complex used as starting material can be obtained by a processes as e.g. shown in the Examples (cf. Example 2) and as described e.g. in EP 12179056.2.

Compounds according to Formula II can also be synthesized in another way: The substituted phenyl-phenanthridine dimer iridium complex (see e.g. example 2.2) is first reacted further with a derivative of the third ligand which contains a functional group (-Q-)Z to result in a monomeric iridium complex. A monomeric iridium complex is e.g. given in Formula I. The monomeric iridium complex is then reacted further with a precursor of Q which contains 1-50 groups which can be reacted with the functional group of the monomeric iridium complex to form covalent bonds; this way after formation of the covalent bonds again a compound according to Formula II is obtained.

In accordance with this process the compounds of Formula II can be e.g. obtained as shown in Scheme 3 below.

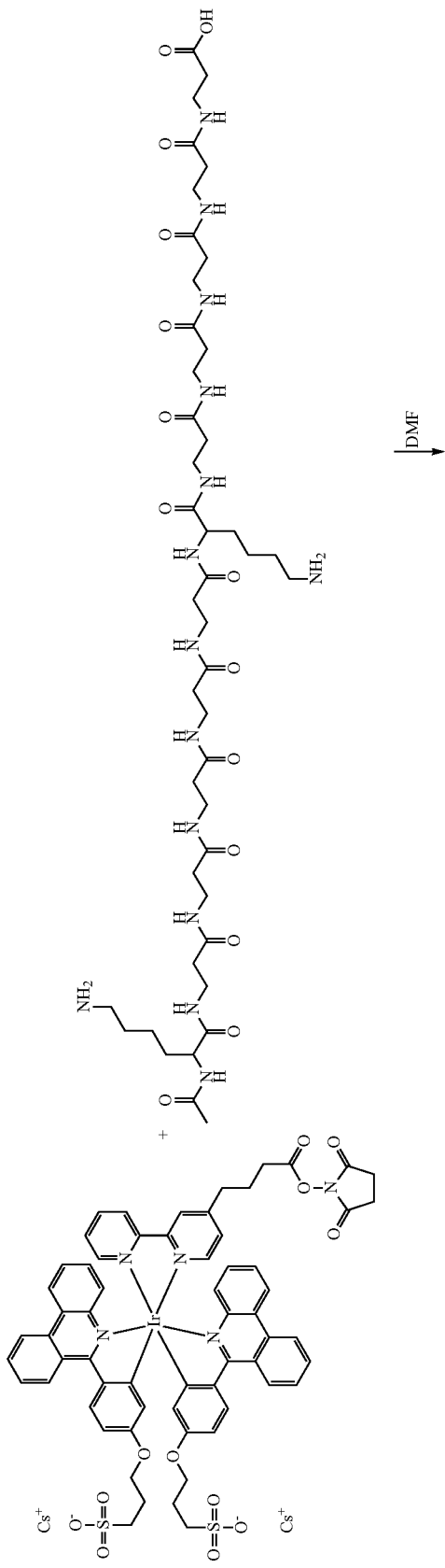
Scheme 3: Synthesis of a compound of Formula II.

-continued
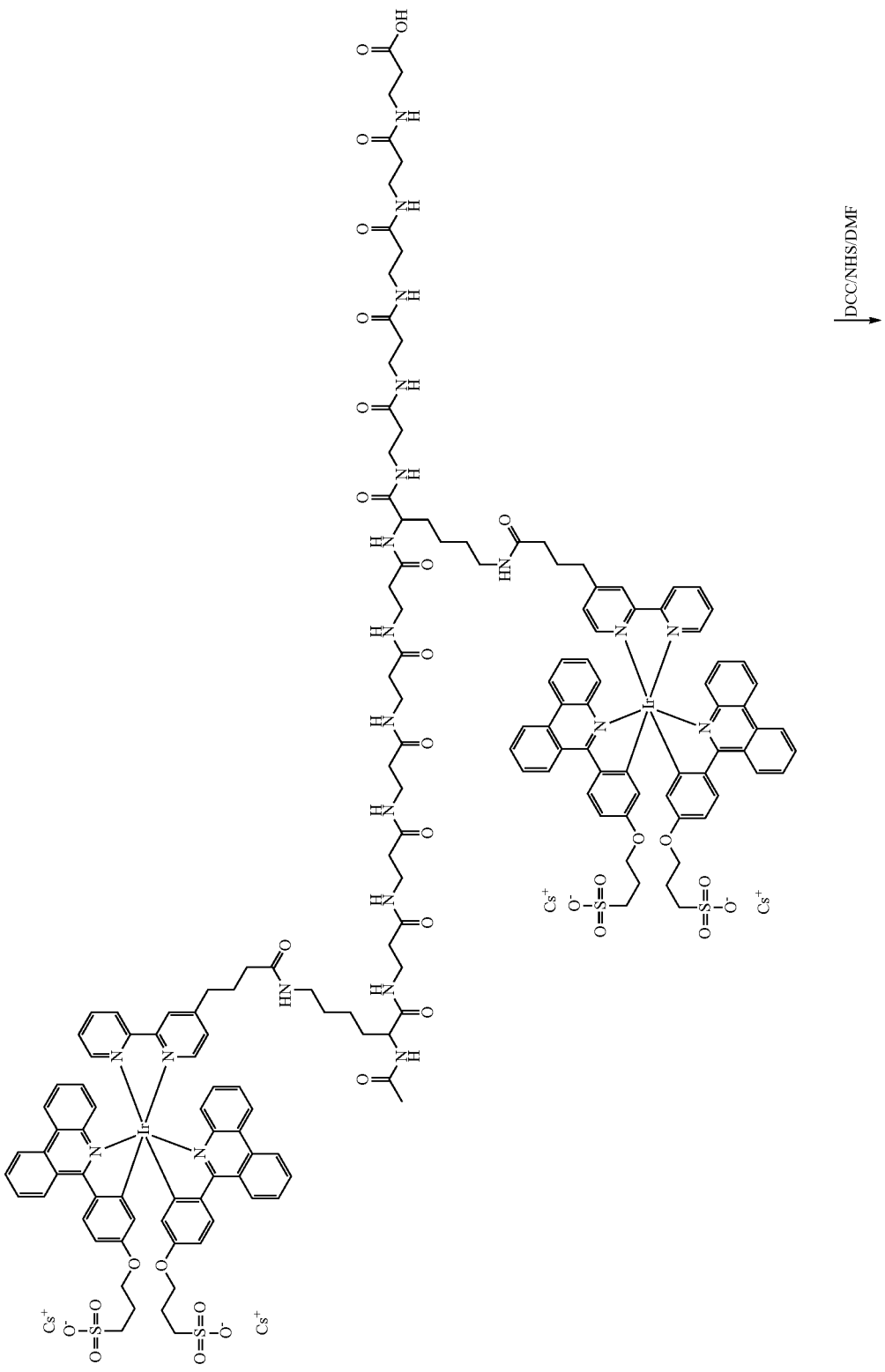
DCC/NHS/DMF

-continued
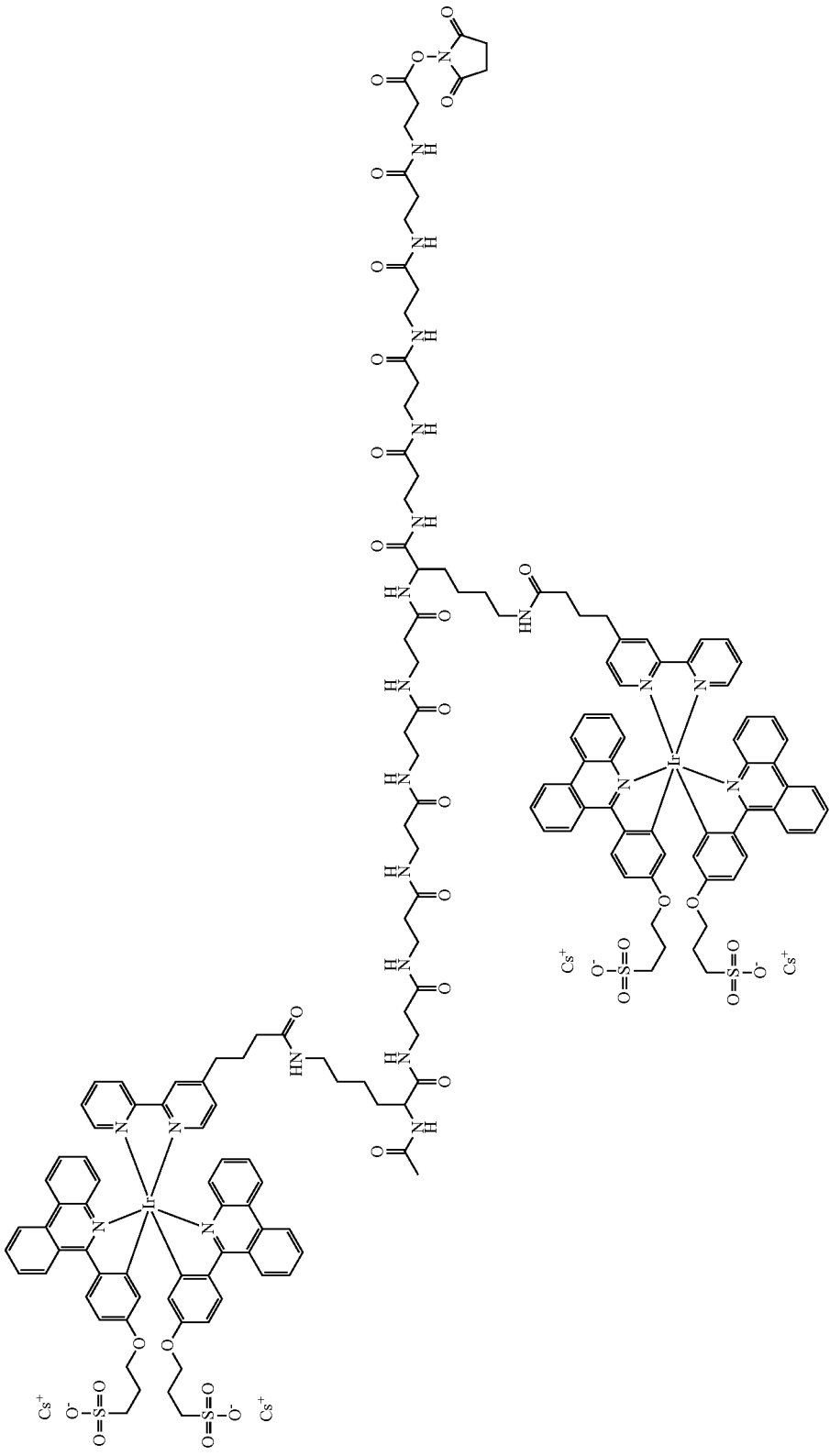

Conjugates Comprising the Novel Compounds of Formulae I or II and Further Aspects of the Invention In one aspect, the present invention relates to a conjugate comprising an iridium-based electrochemiluminescent compound of Formula I, or of Formula II, respectively, as disclosed and defined herein above and covalently bound thereto a biological substance. Examples of suitable biological substances are cells, viruses, subcellular particles, proteins, lipoproteins, glycoproteins, peptides, polypeptides, nucleic acids, peptidic nucleic acids (PNA), oligosaccharides, polysaccharides, lipopoly-saccharides, cellular metabolites, haptens, hormones, pharmacological substances, alkaloids, steroids, vitamins, amino acids and sugars.

In one embodiment the biological substance of a conjugate according to the present invention, i.e., covalently bound to a compound according Formula I, or of Formula II, respectively, is an affinity binding agent. An affinity binding agent is a molecule capable molecular binding to another molecule due to attractive interaction between these molecules that results in a stable association in which the molecules are close to each other. The result of molecular binding is the formation of a molecular complex. The attractive bonding between the components of a complex is normally weaker than in a covalent bond. In the present case, the binding agent is an affinity binding agent which means that it is capable of binding an affinity complex, i.e. a complex stable under the respective conditions, e.g. aequous medium under standard conditions. Molecules that can participate in molecular binding include, but are not limited to, proteins, nucleic acids, carbohydrates, lipids, and small organic molecules such as drugs. Hence the types of complexes that form as a result of molecular binding include: protein-protein, protein-DNA, protein-hormone, protein-drug, antigen-antibody, receptor-ligand, biotin-avidin or streptavidin, nucleic acid-complementary nucleic acid or receptor-receptor (ant)agonist.

As the skilled person will appreciate in a conjugate according to the present invention the functional group Z of the compound according to Formula I, or of Formula II, respectively, has been used to form a covalent bond with a group on the affinity binding agent and is no longer present as such. In case an affinity binding reagent would not in itself contain an appropriate group for binding or reacting with the group Z, such group can be easily introduced into the affinity binding agent by relying on well-established procedures.

In one aspect, the present invention relates to the preparation of a conjugate by reacting the functional group Z of a compound of Formula I or of Formula II with an appropriate reactive group of an affinity binding agent as defined herein with the functional group Z.

This process can be carried out by the skilled person using standard methods known to the skilled person.

In one aspect, the present invention relates to a conjugate obtainable by the process for the preparation of a conjugate described above.

Not wishing to be limited further, but in the interest of clarity, the affinity binding agent may comprise any of the following; an antigen, a protein, an antibody, biotin or biotin analogue and avidin or streptavidin, sugar and lectin, an enzyme, a polypeptide, an amino group, a nucleic acid or nucleic acid analogue and complementary nucleic acid, a nucleotide, a polynucleotide, a peptide nucleic acid (PNA), a polysaccharide, a metal-ion sequestering agent, receptor agonist or a receptor antagonist. For example, the affinity binding agent can be one partner of a specific binding pair, where the other partner of said binding pair is associated with or is the target on a cell surface or an intracellular structure.

In one embodiment, the conjugate comprises a compound of Formula I or Formula II and an affinity binding agent bound thereto selected from the group consisting of a protein, an antigen, an antibody, biotin, a biotin analogue, avidin, streptavidin, sugar, lectin, an enzyme, a polypeptide, an amino group, a nucleic acid, a nucleic acid analogue, a complementary nucleic acid, a nucleotide, a polynucleotide, a peptide nucleic acid (PNA), a polysaccharide, a metal-ion sequestering agent, a receptor agonist or a receptor antagonist.

Preferably an affinity binding agent is, a partner or member of an affinity binding pair, or as it is also called by the skilled person, a partner or member of a specific binding pair.

An affinity binding agent has at least an affinity of $10^7$ 1/mol to its target, e.g. one member of a specific binding pair, like an antibody, to the other member of the specific binding pair, like its antigen. An affinity binding agent preferably has an affinity of $10^8$ 1/mol or even more preferred of $10^9$ 1/mol for its target.

In one embodiment the present invention relates to a conjugate wherein the affinity binding agent is selected from the group consisting of antigen, antibody, biotin or biotin analogue, avidin or streptavidin, sugar, lectin, nucleic acid or nucleic acid analogue and complementary nucleic acid, receptor and ligand.

In one embodiment the present invention relates to a conjugate wherein the affinity binding agent is selected from the group consisting of antibody, biotin or biotin analogue, avidin or streptavidin, and nucleic acid.

In one embodiment, the conjugate comprises a compound of Formula I or Formula II and a protein, an antigen, an antibody, biotin, a biotin analogue, avidin, streptavidin, sugar, lectin, an enzyme, a polypeptide, an amino group, a nucleic acid, a nucleic acid analogue, a complementary nucleic acid, a nucleotide, a polynucleotide, a peptide nucleic acid (PNA), a polysaccharide, a metal-ion sequestering agent, a receptor agonist or a receptor antagonist.

In one embodiment the conjugate according to the present invention comprises covalently linked a compound according to Formula I, or of Formula II, respectively, as disclosed and defined herein above and an affinity binding agent that either is an oligonucleotide or an antibody.

Biotin analogues are aminobiotin, iminobiotin or desthiobiotin.

The term "oligonucleotide" or "nucleic acid" as used herein, generally refers to short, generally single stranded, polynucleotides that comprise at least 8 nucleotides and at most about 1000 nucleotides. In a preferred embodiment an oligonucleotide will have a length of at least 9, 10, 11, 12, 15, 18, 21, 24, 27 or 30 nucleotides. In a preferred embodiment an oligonucleotide will have a length of no more than 200, 150, 100, 90, 80, 70, 60, 50, 45, 40, 35 or 30 nucleotides.

The term oligonucleotide is to be understood broadly and includes DNA and RNA as well as analogues and modifications thereof.

A nucleic acid analogue may for example contain a substituted nucleotide carrying a substituent at the standard bases deoxyadenosine (dA), deoxyguanosine (dG), deoxycytosine (dC), deoxythymidine (dT), deoxyuracil (dU). Examples of such substituted nucleobases are: 5-substituted pyrimidines like 5 methyl dC, aminoallyl dU or dC, 5-(aminoethyl-3-acrylimido)-dU, 5-propynyl-dU or -dC, 5 halogenated-dU or -dC; N substituted pyrimidines like N4-ethyl-dC; N substituted purines like N6-ethyl-dA, N2-ethyl-dG; 8 substituted purines like 8-[6-amino)-hex-1-yl]-8-amino-dG or -dA, 8 halogenated dA or dG, 8-alkyl dG or dA; and 2 substituted dA like 2 amino dA.

A nucleic acid analogue may contain a nucleotide or a nucleoside analogue. I.e. the naturally occurring nucleobases can be exchanged by using nucleobase analogs like 5-nitroindol-d-riboside; 3-nitro-pyrrole-d-riboside, deoxyinosine (dl), deoxyxanthosine (dX); 7 deaza-dG, -dA, -dI or -dX; 7-deaza-8-aza-dG, -dA, -dI or -dX; 8-aza-dA, -dG, -dI or -dX; d-formycin; pseudo dU; pseudo iso dC; 4 thio dT; 6 thio dG; 2 thio dT; iso dG; 5-methyl-iso-dC; N8-linked 8-aza-7-deaza-dA; 5,6-dihydro-5-aza-dC; and etheno-dA or pyrrolo-dC. As obvious to the skilled person, the nucleobase in the complementary strand has to be selected in such manner that duplex formation is specific. If, for example, 5-methyl-iso-dC is used in one strand (e.g. (a)) iso dG has to be in the complementary strand (e.g. (a')).

In a nucleic acid analogue the oligonucleotide backbone may be modified to contain substituted sugar residues, sugar analogs, modifications in the internucleoside phosphate moiety, and/or be a PNA.

An oligonucleotide may for example contain a nucleotide with a substituted deoxy ribose like 2'-methoxy, 2'-fluoro, 2'-methylseleno, 2'-allyloxy, 4'-methyl dN (wherein N is a nucleobase, e.g., A, G, C, T or U).

Sugar analogs are for example xylose; 2',4' bridged ribose like (2'-O, 4'-C methylene)-(oligomer known as LNA) or (2'-O, 4'-C ethylene)-(oligomer known as ENA); L-ribose, L-d-ribose, hexitol (oligomer known as HNA); cyclohexenyl (oligomer known as CeNA); altritol (oligomer known as ANA); a tricyclic ribose analog where C3' and C5' atoms are connected by an ethylene bridge that is fused to a cyclopropane ring (oligomer known as tricycloDNA); glycerin (oligomer known as GNA); glucopyranose (oligomer known as Homo DNA); carbaribose (with a cyclopentane instead of a tetrahydrofuran subunit); hydroxymethyl-morpholine (oligomers known as morpholino DNA)

A great number of modifications of the internucleosidic phosphate moiety are also known not to interfere with hybridization properties and such backbone modifications can also be combined with substituted nucleotides or nucleotide analogs. Examples are phosphorothioate, phosphorodithioate, phosphoramidate and methylphosphonate oligonucleotides.

PNA (having a backbone without phosphate and d-ribose) can also be used as a DNA analog.

The above mentioned modified nucleotides, nucleotide analogs as well as oligonucleotide backbone modifications can be combined as desired in an oligonucleotide in the sense of the present invention.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or non-proteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light-chain and heavy-chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The subunit structures and three-dimensional configurations of different classes of immunoglobulins are well known and described generally in, for example, Abbas et al., Cellular and Mol. Immunology, 4th ed., W.B. Saunders, Co. (2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen-binding region thereof. Examples of antibody fragments include Fab, Fab', F(ab')2, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields a F(ab')2 fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody-hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Single-chain Fv" or "scFv" antibody fragments comprise the VH and VL domains of an antibody, wherein these domains are present in a single polypeptide chain. Generally, the scFv polypeptide further comprises a polypeptide linker between the VH and VL domains that enables the scFv to form the desired structure for antigen binding. For a review of scFv, see, e.g., Plueckthun, n: The Pharmacology of Monoclonal Antibodies, Vol. 113, Rosenburg and Moore (eds.), Springer-Verlag, New York (1994) pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 0 404 097; WO 1993/01161; Hudson, P. J. et al., Nat. Med. 9 (2003) 129-134; and Holliger, P. et al., PNAS USA 90 (1993) 6444-6448. Triabodies and tetrabodies are also described in Hudson, P. J. et al., Nat. Med. 9 (2003) 129-134.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

As mentioned, the compounds and conjugates as disclosed herein have quite favorable properties. For example the disclosed compounds or conjugates, respectively, show a high ECL efficiency. This high efficiency is also present if the corresponding measurements are performed in an aqueous system as compared to many ECL-labels that only have shown high ECL-efficiency when analyzed in an organic solvent. E.g., many OLED dyes usually are analyzed in acetonitrile and either are not soluble in an aequeous solution or, if soluble, do not show efficient electrochemiluminescence in an aequeous solution.

In one preferred embodiment the present invention relates to the use of a compound or of a conjugate, respectively, as disclosed in the present invention for performing an electrochemiliuminescense reaction in an aqueous solution. An aqueous solution is any solution comprising at least 90% water (weight by weight). Obviously such aqueous solution may contain in addition ingredients like buffer compounds, detergents and for example tertiary amines like tripropylamine as electron donor in the ECL reaction.

In one aspect, the present invention relates to the use of a compound or of a conjugate, respectively, as disclosed in the present invention in an electrochemiluminescence based detection method.

In one aspect, the present invention relates to the use of a compound or of a conjugate, respectively, as disclosed in the present invention in the detection of an analyte.

An analyte according to the present invention may be any inorganic or organic molecule, including any biological substance of interest. Examples of suitable biological substances that represent an analyte in the sense of the present invention are cells, viruses, subcellular particles, proteins, lipoproteins, glycoproteins, peptides, polypeptides, nucleic acids, oligosaccharides, polysaccharides, lipopoly-saccharides, cellular metabolites, haptens, hormones, pharmacological substances, alkaloids, steroids, vitamins, amino acids and sugars.

The analyte may be selected from the group consisting of a polypeptide, a carbohydrate, and an inorganic or organic drug molecule.

A polypeptide or protein is a molecule that is essentially composed of amino acids and that has at least two amino acids linked by peptidic linkage. In case the analyte of interest to be investigated in a method disclosed here, the polypeptide preferably will consist of at least 5, 6, 7, 8, 9, 10, 12, 15, 20, 25, and 30 to up to about 10,000 amino acids. Preferably the polypeptide will contain from 5 to 2,000, also preferred from 10 to 1,000 amino acids.

In case the analyte is a nucleic acid, these nucleic acids preferably are naturally occurring DNA or RNA oligonucleotides.

In one aspect, the present invention relates to a method for measuring an analyte by an in vitro method, the method comprising the steps of (a) providing a sample suspected or known to comprise the analyte, (b) contacting said sample with a conjugate according between an affinity binding agent and a compound according to Formula I or of Formula II, respectively, as disclosed in the present invention under conditions appropriate for formation of an analyte conjugate complex, and (c) measuring the complex formed in step (b) and thereby obtaining a measure of the analyte.

In one embodiment measuring an analyte means detecting the amount of an analyte in a sample.

In one embodiment the measurement in the above method for detection of an analyte is performed by using an electrochemiluminescence based detection procedure. Also preferred the method is practiced in an aqueous solution.

The following examples are provided to aid the understanding of the present invention, the true scope of which is set forth in the appended claims. It is understood that modifications can be made in the procedures set forth without departing from the spirit of the invention.

All patents and publications identified herein are incorporated herein by reference in their entirety.

EXAMPLES

Example 1

Synthesis of substituted phenyl-phenanthridines

Example 1.1

General Procedure for the synthesis of substituted 2-aminobiphenyls

With the Suzuki-Miyaura coupling reaction as described by Youn, S. W., in Tetrahedron Lett. 50 (2009) 4598-4601, between commercially available 2-bromoaniline derivatives and the corresponding arylboronic acid the appropriate 2-aminobiphenyls can be synthesized, which are required for further reactions to phenanthridines.

Typical Procedure:

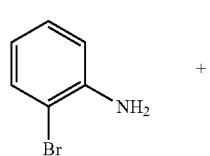

+

-continued

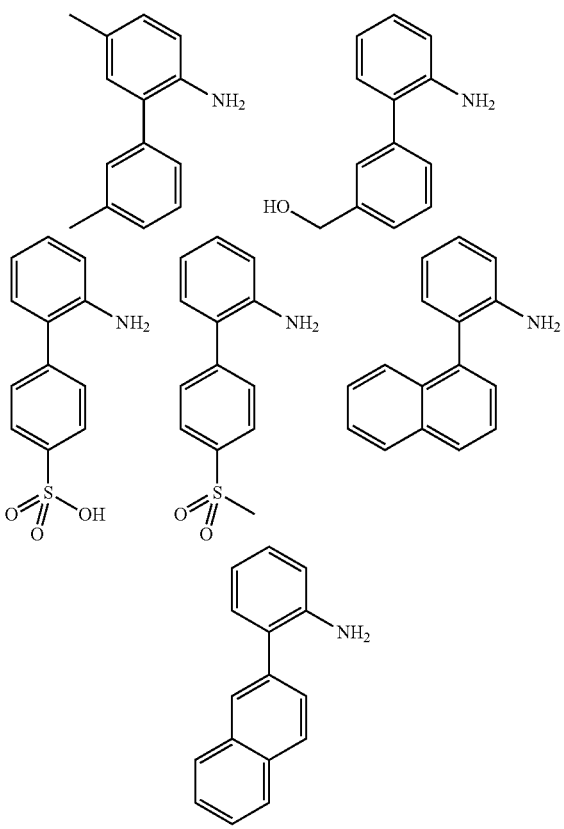

a: 10 mol % PdCl$_2$(PPh$_3$)$_2$, K$_2$CO$_3$, DMF/H$_2$O (5/1), 80° C., 24 h

Other Examples

Example 1.2

General Procedure for the Synthesis of Substituted Phenanthridines

To the ice-cooled solution of 2-arylaniline 1 (0.01 mol) in chloroform (20 ml) was added aryl acid chloride 2 (0.01 mol) and stirred under inert condition for 30 min at room temperature. The resulting mixture was refluxed with stirring for the next 2 hours. The reaction mixture was treated by the dropwise addition of pyridine (0.02 mol in 10 ml chloroform) over a period of 60 minutes. The mixture was allowed to cool to room temperature and stirred overnight. The mixture was washed well with 0.5 M HCl, dried over MgSO₄ and concentrated in vacuum. The crude product was purified by flash chromatography on silica gel, 3:2 hexane/ethyl acetate to give pure product 3 in 66% yield.

Benzamido-2-biphenyl 3 (0.01 mol) and POCl₃ (5 ml) in 20 ml of toluene were refluxed and stirred under nitrogen for 18 hours, following the procedure described by Lion, C., in Bull. Soc. Chim. Belg. 98 (1989) 557-566. The cooled reaction mixture was diluted with CH₂Cl₂ (30 ml) and poured into ice, washed with 25% NH₄OH and distilled water. The organic layer was dried over MgSO₄ and concentrated in vacuo, followed by flash chromatography (silica gel, 1:1 hexane/ethyl acetate) gave the product 4, 6-phenylphenanthridine.

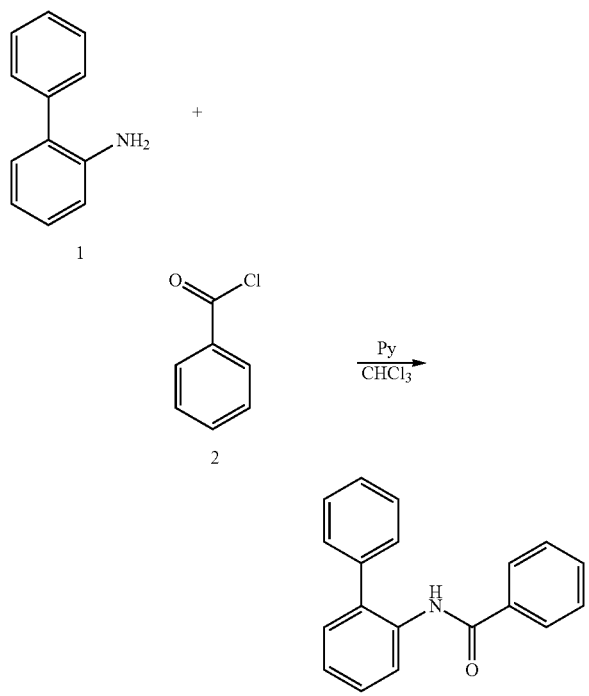

Yield: 52%. White solid. $^1$H NMR (CDCl₃, 400 MHz) δ 7.54-7.85 (m, 9H), 8.10 (d, J=8.0 Hz, 1H), 8.28 (d, J=7.9 Hz, 1H), 8.62 (d, J=8.4 Hz, 1H), 8.67 (d, J=8.4 Hz, 1H).

Using 2-naphthalen-2-yl-phenylamine instead of 2-arylaniline:

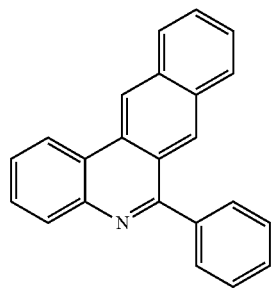 [SMILES: c1ccc(-c2nc3ccccc3c3cc4ccccc4cc23)cc1]

$^1$H-NMR (400 MHz, CDCl₃) δ 8.64 (d, J=9.1 Hz, 2H), 8.29 (d, J=8.1 Hz, 1H), 8.16 (d, J=8.92 Hz, 1H), 7.92 (d, J=7.48 Hz, 1H), 7.79-7.75 (m, 2H), 7.69 (t, J=14.0, 8.2 Hz, 1H), 7.63-7.61 (m, 2H), 7.53-7.46 (m, 4H), 7.19 (t, J=14.3, 7.2 Hz, 1H).

MS: [1\4+H]⁺306.3

Using naphthalene-carbonyl chloride instead of phenyl acid chloride yields:

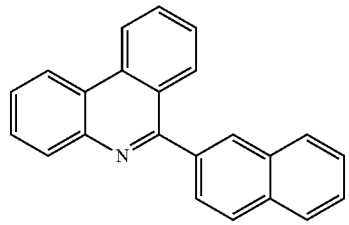 [SMILES: c1ccc2cc(-c3nc4ccccc4c4ccccc34)ccc2c1]

$^1$H-NMR (400 MHz, CDCl₃) δ 8.74 (d, J=8.3 Hz, 1H), 8.65 (d, J=8.1 Hz, 1H), 8.27 (d, J=8.1 Hz, 1H), 8.23 (s, 1H), 8.15 (d, J=8.3 Hz, 1H), 8.03 (d, J=8.4 Hz, 1H), 7.97-7.94 (m, 2H), 7.90-7.85 (m, 2H), 7.80-7.69 (m, 2H), 7.62 (t, J=14.2, 7.1 Hz, 1H), 7.59-7.55 (m, 2H).

MS: [M+H]⁺ 306.3

Example 1.3

Procedure for the synthesis of 6-(2-sulfophenyl)phenanthridine

The 6-(2-sulfophenyl)phenanthridine can be synthesized by gentle heating of arylaniline (0.01 mol) with 2-sulfobenzoic acid cyclic anhydride (0.01 mol) in CH₃CN for 6 hours using the procedure as described by Nicolai, E., in Chem. Pharm. Bull. 42 (1994) 1617-1630.

After purification the product can be converted to the appropriate phenanthridine based on the method described in example 1.2.

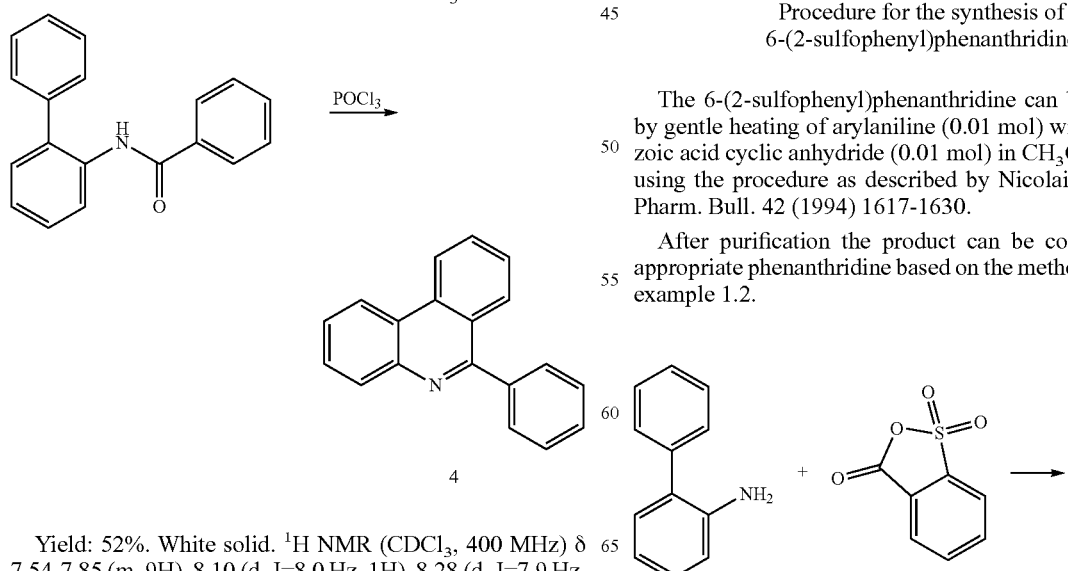

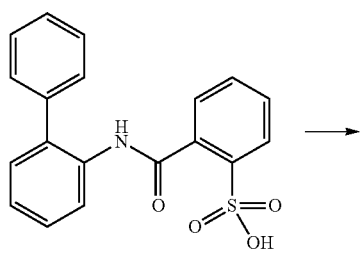

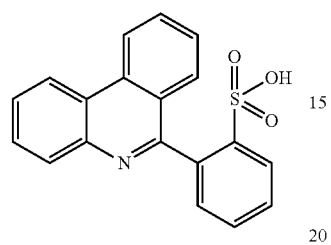

$^1$H-NMR (400 MHz, CDCl$_3$) δ 8.92 (d, J=8.7 Hz, 1H), 8.75 (d, J=1.9 Hz, 1H), 8.68 (d, J=7.0 Hz, 1H), 8.35 (dd, J=8.7, 2.0 Hz, 1H), 8.30 (d, J=7.2 Hz, 1H), 7.89 (t, J=15.3, 7.1 Hz, 1H), 7.81-7.73 (m, 3H), 7.64-7.56 (m, 3H) 3.12 (s, 3H).

MS: [M+H]+ 334.3

The 6-(4-methylsulfophenyl)phenanthridine can be also prepared by following the procedure described by Cymerman, J., in J. Chem. Soc. (1949) 703-707.

Example 1.5

Synthesis of 6-[4-(2-{2-[2-(2-methoxy-ethoxy)-ethoxy]-ethoxy}-ethoxy)-phenyl]-phenanthridine

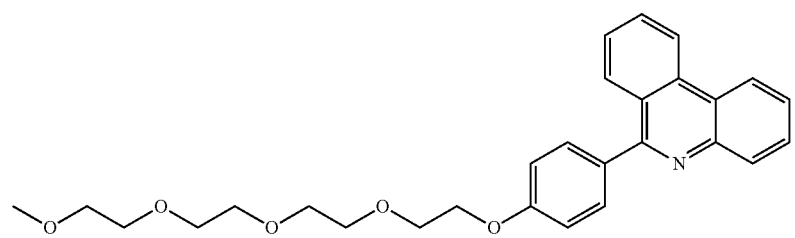

Example 1.4

Procedure for the synthesis of 6-phenyl-alkylsulfonyl phenanthridine

The 6-phenyl-alkylsulfonyl phenanthridine can be synthesized by gentle heating of alkylsulfonyl-arylaniline (0.01 mol) with benzoic acid chloride (0.01 mol) in chloroform using the procedure as described by Lion, C., in Bull. Soc. Chim. Belg. 98 (1989) 557-566, see example 1.2.

After purification the product can be converted to the appropriate phenanthridine based on the method described in example 1.2.

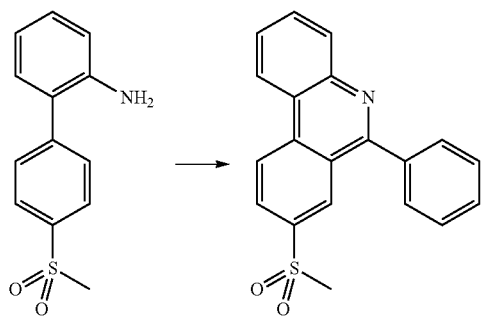 [SMILES: CS(=O)(=O)c1ccc(-c2ccccc2N)cc1 ; CS(=O)(=O)c1ccc2c(c1)c(-c1ccccc1)nc1ccccc12]

Synthesis of 2,5,8,11-tetraoxatridecan-13-ol tosylate

Procedure: (JACS, 2007, 129, 13364) To a solution of 2,5,8,11-tetraoxatridecan-13-ol (7 g, 33.6 mmol) and triethylamine (4.9 ml, 35.3 mmol) in dry CH$_2$Cl$_2$ (100 ml), 4-toluenesulfonyl chloride (6.7 g, 35.3 mmol) and DMAP (120 mg) were added. The mixture was stirred at room temperature for 20 h. The reaction mixture was washed with 80 mL of HCl (1M) and then water. The extract was dried over anhydrous MgSO$_4$, filtrated, and the filtrate was evaporated. The residue was used in the next step without further purification.

Yield: 11.0 g (90%)

NMR:

$^1$H NMR (400 MHz, CDCl$_3$) δ 7.75-7.64 (m, 2H), 7.31-7.26 (m, 2H), 4.16-4.06 (m, 2H), 3.62 (m 2H), 3.59-3.40 (m, 10H), 3.30 (s, 3H), 2.38 (s, 3H).

$^{13}$C{$^1$H} NMR (101 MHz, CDCl$_3$) δ 144.75 (s), 132.90 (s), 129.77 (s), 127.8 (s), 71.82 (s), 70.60 (s), 70.48 (s), 70.47 (s), 70.41 (s), 70.39 (s), 69.23 (s), 68.55 (s), 58.90 (s), 21.53 (s).

Synthesis of 4-PEG4-benzoic acid ethyl ester

Procedure: (JACS, 2007, 129, 13364) A mixture of compound ethyl 2,5,8,11-tetraoxatridecan-13-yl 4-methylbenzenesulfonate (8.1 g, 22.3 mmol), 4-hydroxybenzoic acid ethyl ester (3.7 g, 22.3 mmol), K$_2$CO$_3$ (15.4 g, 111.5 mmol) and 18-crown-6 (0.59 g, 2.2 mmol) was refluxed in acetone (120 ml) for 22 h. The reaction mixture was concentrated and extracted with ethyl acetate. The extract was washed with H$_2$O, dried over anhydrous MgSO$_4$, and filtrated. The filtrate was evaporated to dryness and the residue was purified by column chromatography on silica gel (dichloromethane/methanol=100:1) to obtain the compound (1.93 g, 88%).

Yield: 7 g (88%)

NMR:

$^1$H NMR (400 MHz, CDCl$_3$) δ 8.01-7.84 (m, 2H), 6.96-6.85 (m, 2H), 4.29 (q, J=7.1 Hz, 2H), 4.12 (dd, J=5.4, 4.3 Hz, 2H), 3.82 (dd, J=5.4, 4.2 Hz, 2H), 3.71-3.56 (m, 10H), 3.51-3.45 (m, 2H), 3.32 (s, 3H), 1.32 (t, J=7.1 Hz, 3H).

$^{13}$C{$^1$H} NMR (101 MHz, CDCl$_3$) δ 166.29 (s), 162.47 (s), 131.45 (s), 123.01 (s), 114.11 (s), 71.90 (s), 70.84 (s), 70.60 (s), 70.59 (s), 70.58 (s), 70.48 (s), 69.51 (s), 67.54 (s), 60.57 (s), 58.98 (s), 14.35 (s).

MS(+):

[M+Na$^+$]$^+$=calc. 379.1727, found 379.1743.

Synthesis of 4-PEG4-benzoic acid

Procedure: (JACS, 2007, 129, 13364) A mixture of compound ethyl 4-(2,5,8,11-tetraoxatridecan-13-yloxy)benzoate (7 g, 19.6 mmol), and KOH (2.3 g, 41.24 mmol) in 200 mL of EtOH/H$_2$O (1:1 v/v) was refluxed overnight. After cooling down, the mixture was neutralized with HCl (2N). The resulting mixture was extracted with EtOAc and evaporated to dryness. The resulting white solid was recrystallized in EtOAc/hexane.

Yield: 5.3 g (85%)

NMR:

$^1$H NMR (300 MHz, CDCl$_3$) δ 11.17 (s, 1H), 8.14-7.89 (m, 2H), 7.03-6.75 (m, 2H), 4.29-4.02 (m, 2H), 3.92-3.81 (m, 2H), 3.78-3.57 (m, 10H), 3.57-3.46 (m, 2H), 3.35 (s, 3H).

$^{13}$C{$^1$H} NMR (75 MHz, CDCl$_3$) δ 171.46 (s), 163.24 (s), 132.30 (s), 121.98 (s), 114.33 (s), 71.96 (s), 70.91 (s), 70.67 (s), 70.66 (s), 70.64 (s), 70.54 (s), 69.55 (s), 67.66 (s), 59.08 (s).

MS(−):

[M−H]$^-$=calc. 327.1438, found 327.1456.

Synthesis of N-biphenyl-2-yl-4-(2-{2-[2-(2-methoxy-ethoxy)-ethoxy]-ethoxy}-ethoxy)-benzamide Procedure: To a solution of 4-(2,5,8,11-tetraoxatridecan-13-yloxy)benzoic acid (3 g, 9.14 mmol), 0.2 mL of DMF in 30 mL dry DCM at 0° C., oxalyl chloride (1.05 mL, 12.34 mmol) was added. The reaction mixture was stirred at 0° C. for 1 h. The solution was concentrated to dryness. The oily residue was used without further purification in the next step.

A solution of 2-phenylaniline (1.6 g), pyridine (2.4 mL) in chloroform (80 mL) under inert atmosphere was cooled down to 0° C. (phenyl-4-(2,5,8,11-tetraoxatridecan-13-yloxy)benzoyl chloride (3.1 g, 9.14 mmol) in 20 mL was slowly added to the solution and the final mixture allowed to reach room temperature. The solution was refluxed for 2 h and stirred overnight at room temperature. The reaction mixture was extracted with HCl (1 M, 2×100 mL), NaHCO$_3$ (100 mL) and water (50 mL). The organic phase was dried with MgSO$_4$ and purified by chromatography in silica gel (EtOAc/hexane).

Yield: 4.1 (90%)

NMR:

$^1$H NMR (400 MHz, CDCl$_3$) δ 8.49 (dd, J=8.3, 0.9 Hz, 1H), 7.94 (s, 1H), 7.61-7.35 (m, 9H), 7.33-7.25 (m, 1H), 7.19 (m, 1H), 6.91-6.84 (m, 2H), 4.16-4.10 (m, 2H), 3.85 (m, 2H), 3.77-3.58 (m, 10H), 3.56-3.49 (m, 2H), 3.36 (s, 3H).

$^{13}$C{$^1$H} NMR (101 MHz, CDCl$_3$) δ 164.56 (s), 161.65 (s), 138.18 (s), 135.12 (s), 132.32 (s), 129.97 (s), 129.39 (s), 129.22 (s), 128.66 (s), 128.57 (s), 128.16 (s), 127.13 (s), 124.18 (s), 121.23 (s), 114.57 (s), 71.95 (s), 70.89 (s), 70.64 (s), 70.63 (s), 70.54 (s), 69.54 (s), 67.63 (s), 59.04 (s), 53.51 (s).

MS(+):

[M+H]$^+$=calc. 480.2386 found. 480.2383; [M+Na]$^+$=calc. 502.2200, found 502.2204.

Synthesis of 6-[4-(2-{2-[2-(2-methoxy-ethoxy)-ethoxy]-ethoxy}-ethoxy)-phenyl]-phenanthridine Procedure: N-Biphenyl-2-yl-4-(2-{2-[2-(2-methoxy-ethoxy)-ethoxy]-ethoxy}-ethoxy)-benzamide (4 g, 8.34 mmol), POCl$_3$ (10 ml) in 10 ml toluene were refluxed for 20 h. The mixture was cooled down to room temperature, and 100 ml of dichloromethane were added. The solution was poured into ice and the mixture neutralized with NH$_4$OH (20%). The organic phase was extracted and washed successively with destilled water and brine, and dried over MgSO$_4$. The resulting solution was purified by flash chromatography (silica gel, in ethyl acetate/hexane 1:1, R$_f$=0.14).

Yield: 1 g (25%)

NMR:

$^1$H NMR (300 MHz, CDCl$_3$) δ 8.68 (d, J=8.3 Hz, 1H), 8.59 (dd, J=8.1, 1.4 Hz, 1H), 8.23 (dd, J=8.1, 1.1 Hz, 1H), 8.15 (dd, J=8.3, 0.7 Hz, 1H), 7.84 (ddd, J=8.3, 7.1, 1.3 Hz, 1H), 7.79-7.57 (m, 5H), 7.15-7.03 (m, 2H), 4.29-4.19 (m, 2H), 3.93-3.90 (m, 2H), 3.80-3.60 (m, 12H), 3.59-3.49 (m, 2H), 3.37 (s, 3H).

$^{13}$C{$^1$H} NMR (75 MHz, CDCl$_3$) δ 160.92 (s), 159.45 (s), 143.84 (s), 133.59 (s), 131.26 (s), 130.61 (s), 130.26 (s), 129.05 (s), 128.90 (s), 127.19 (s), 126.85 (s), 125.39 (s), 123.70 (s), 122.29 (s), 122.01 (s), 114.68 (s), 72.02 (s), 70.97 (s), 70.74 (s), 70.72 (s), 70.69 (s), 70.62 (s), 69.80 (s), 67.68 (s), 59.15 (s).

MS (+) JM358-F5, [M+H]$^+$ calc=462.2280, found 462.2275.

Synthesis of 3-(4-phenanthridin-6-yl-phenoxy)-propane-1-sulfonate caesium salt

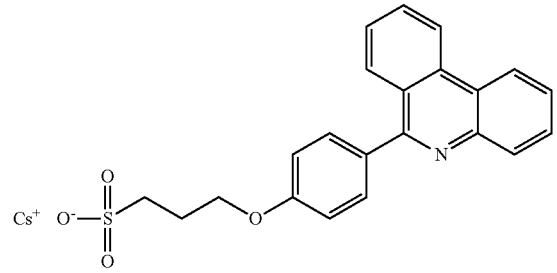

6-(4-Methoxyphenyl)phenanthridine was prepared by cyclisation of the N-(biphenyl-2-yl)-4-methoxybenzamide (2 g, 6.59 mmol) following the procedure as described above. The compound was purified by chromatography in dichloromethane/hexane (gradient 1:5 to 1:1).

Yield: 87%.

NMR: $^1$H NMR (300 MHz, DMSO) δ 8.94 (d, J=8.2 Hz, 1H), 8.84 (dd, J=8.2, 1.2 Hz, 1H), 8.18-8.05 (m, 2H), 7.97 (ddd, J=8.3, 7.1, 1.3 Hz, 1H), 7.86-7.62 (m, 5H), 7.23-7.07 (m, 2H), 3.88 (s, 3H).

$^1$H NMR (300 MHz, CDCl$_3$) δ 8.70 (d, J=8.3 Hz, 1H), 8.61 (dd, J=8.1, 1.3 Hz, 1H), 8.28 (d, J=8.0 Hz, 1H), 8.18 (dd,

J=8.3, 0.7 Hz, 1H), 7.86 (ddd, J=8.3, 7.1, 1.3 Hz, 1H), 7.81-7.56 (m, 5H), 7.18-7.02 (m, 2H), 3.92 (s, 3H).

$^{13}$C NMR (75 MHz, CDCl$_3$) δ 160.95 (s), 160.33 (s), 143.72 (s), 133.67 (s), 132.12 (s), 131.36 (s), 130.71 (s), 130.20 (s), 129.13 (s), 128.97 (s), 127.23 (s), 126.92 (s), 125.40 (s), 123.73 (s), 122.33 (s), 122.03 (s), 114.03 (s), 55.57 (s).

MS [ESI-MS (+)]: [M+H$^+$]$^-$ found 286.1231, calc. 286.1226

4-Phenanthridin-6-yl-phenol: Deprotection of the 6-(4-methoxyphenyl)phenanthridine was achieved by using HBr. A suspension of 6-(4-methoxyphenyl)phenanthridine (1 g, 3.5 mmol) in 15 mL (HBr, 47%) was refluxed at 100° C. for 12 h. The mixture was cooled down to room temperature, poured into ice-water and neutralized with Na$_2$CO$_3$. The resulting precipitate was filtered off and washed with water and Et$_2$O. The solid was purified by chromatography column using dichloromethane/MeOH. Yield: 90%.

NMR: $^1$H NMR (300 MHz, DMSO) δ 9.84 (s, 1H), 8.92 (d, J=8.2 Hz, 1H), 8.82 (dd, J=8.2, 1.2 Hz, 1H), 8.20-8.11 (m, 1H), 8.08 (dd, J=8.1, 1.2 Hz, 1H), 8.02-7.88 (m, 1H), 7.84-7.64 (m, 3H), 7.64-7.49 (m, 2H), 7.06-6.89 (m, 2H).

MS [ESI-MS (−)]: [M−H$^+$]$^-$ found 270.0922, calc. 270.0924

To a solution of 4-(phenanthridin-6-yl)phenol (320 mg, 1.18 mmol) in DMF (4 ml), Cs$_2$CO$_3$ (482.2 mg, 1.48 mmol) and 1,3-propylsultone (159 mg, 1.30 mmol) were added. The reaction mixture was stirred overnight at room temperature. The reaction mixture was concentrated to dryness and the residue was purified by chromatography column (silica) using dichloromethane/MeOH (gradient 10:1 to 5:1). Yield: 72%

NMR: 1H NMR (300 MHz, DMSO-d$_6$) δ 8.98-8.87 (m, 1H), 8.83 (dd, J=7.9, 1.6 Hz, 1H), 8.12 (m, 2H), 7.97 (ddd, J=8.3, 7.0, 1.3 Hz, 1H), 7.85-7.69 (m, 3H), 7.67 (d, J=8.6 Hz, 2H), 7.14 (d, J=8.7 Hz, 2H), 4.19 (t, J=6.5 Hz, 2H), 2.64-2.57 (m, 2H), 2.15-1.97 (m, 2H).

MS [EI-MS (−)]: [M−Cs$^+$]$^-$ calc 392.0956. found 392.0962.

Example 2

General Procedure for the Synthesis of Chloro-Cross-Linked Dimer Complex

The general procedure was published by Nonoyama, M., J. Organomet. Chem. 86 (1975) 263-267.

The iridium dimers were synthesized as follow: IrCl$_3$.3H$_2$O and 2.5 equiv of 6-phenylphenanthridine were heated at 120° C. for 18 h under nitrogen in 2-ethoxyethanol/water mixture (3:1, v/v). After being cooled to room temperature the precipitate was filtered off and successively washed with methanol and Et$_2$O, dried to afford the desired dimer.

Example 2.1

Complex with Unsubstituted Phenylphenanthridine

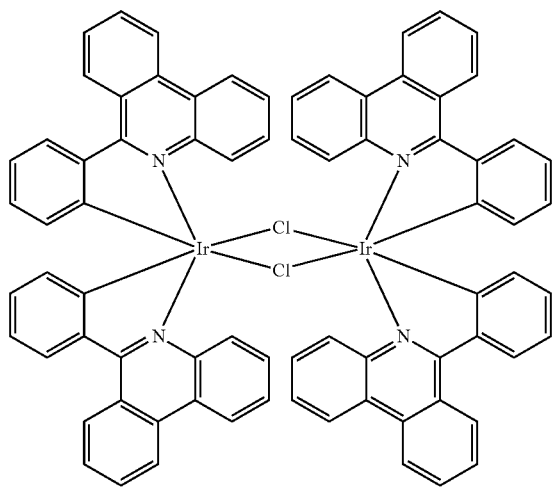

[(6-phenylphenanthridine)$_2$IrCl]$_2$.

Yield: 71%. Brown solid. $^1$H NMR (DMSO-d$_6$, 400 MHz) δ 6.45 (d, J=6.8, 4H), 6.58 (t, J=7.1, 13.9 Hz, 4H), 6.95 (t, J=7.1, 14.2 Hz, 4H), 7.56 (t, J=7.4, 16.0 Hz, 4H), 7.68 (t, J=8.1, 16.2 Hz, 4H), 7.93 (t, J=8.0, 14.6 Hz, 4H), 8.07-8.13 (m, 8H), 8.80 (d, J=7.3 Hz, 4H), 8.93-9.01 (m, 12H).

Example 2.2

Complex with Substituted Phenylphenanthridine

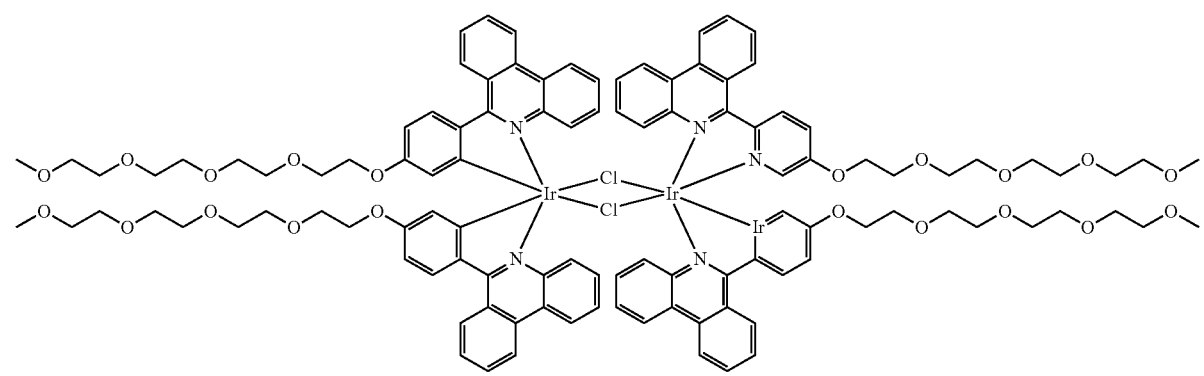

A mixture of 6-[4-(2-{2-[2-(2-methoxy-ethoxy)-ethoxy]-ethoxy}-ethoxy)-phenyl]-phenanthridine (1 g, 2.16 mmol), IrCl$_3$.3H$_2$O (346 mg, 0.98 mmol) in 16 ml of 2-EtOEtOH: H$_2$O (12:4) was refluxed overnight under nitrogen atmosphere. The reaction mixture was cooled down to room temperature and 60 ml of water were added to obtain an oily precipitate. The supernatant was discarded and 50 ml of water were added to the residue. The mixture was stirred for 1 h to obtain a red-brownish precipitate. The solid was filtrated and washed with water (50 ml) and Et$_2$O (30 ml). The brown solid was dissolved in the smaller amount of dichloromethane and precipitated upon addition of Et$_2$O. It was used in the next step without further purification.

Yield: 550 mg (50%)

NMR:

$^1$H NMR (300 MHz, CDCl$_3$) δ 8.74 (d, J=8.1 Hz, 4H), 8.36 (dd, J=8.0, 5.2 Hz, 8H), 7.90 (dd, J=14.7, 7.7 Hz, 8H), 7.81 (d, J=9.0 Hz, 4H), 7.79-7.67 (m, 4H), 6.78-6.65 (m, 4H), 6.32 (dd, J=8.8, 2.5 Hz, 4H), 5.89-5.83 (m, 4H), 5.28 (d, J=2.5 Hz, 4H), 3.67-3.10 (m, 100H, PEG Chain, contains some impurities)

MS(ESI-MS(+)):

[M+2Na$^+$]$^{2+}$ calc. 1171.3463, found 1171.3473; [(C^N)$_2$Ir]$^+$=calc. 1113.3877, found 1113.3892.

Synthesis of bis-iridium complex with 3-(4-phenanthridin-6-yl-phenoxy)-propane-1-sulfonate caesium salt

Example 3

Synthesis of Ir(6-phenylphenanthridine)$_2$ carboxypropylphenyl-bipyridine complex as chloride salt

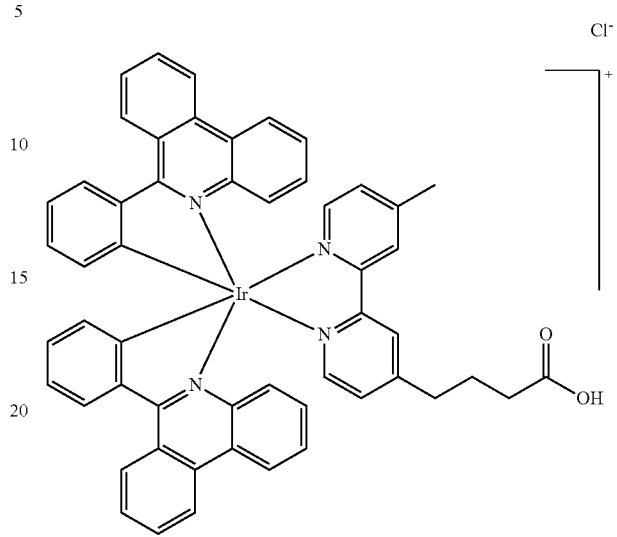

A mixture of dimer [(6-phenylphenanthridine)$_2$IrCl]$_2$ (163 mg, 0.110 mmol), 4-(4-methyl-2,2-bipyridine-4'-yl)-butyric acid (60 mg, 0.232 mmol) in 2-ethoxyethanol (15 ml) was heated at reflux under nitrogen atmosphere overnight. The product was precipitated with water and filtered off. The

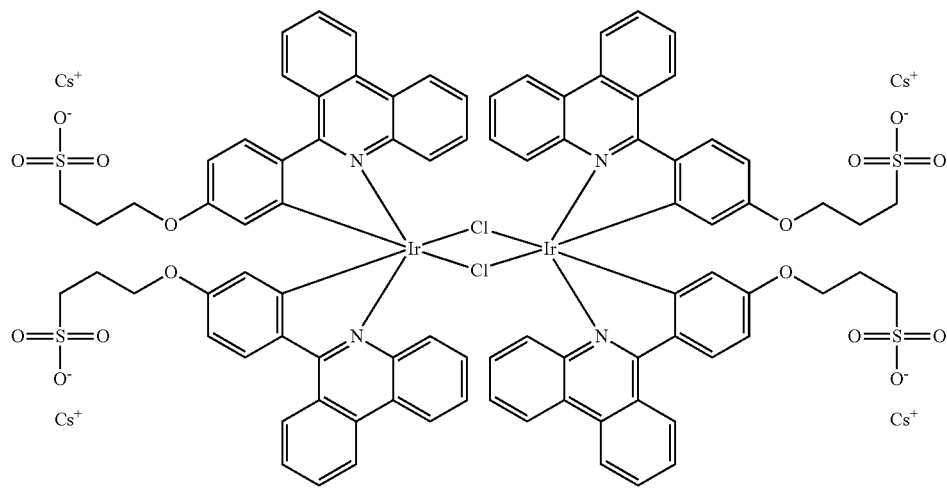

A mixture of the ligand caesium 3-(4-(phenanthridin-6-yl)phenoxy)propane-1-sulfonate (500 mg, 0.92 mmol) and IrCl$_3$ (159.5 mg, 0.45 mmol) in 2-EtOEtOH:water (3:1, 16 ml) mixture, was refluxed under nitrogen atmosphere for 36 h. The reaction mixture was filtered, and the filtrate was concentrated to dryness. The residue was used in the next step without further purification.

MS [ESI-MS(−)]: [Ir(C^N)$_2$−2Cs$^+$]$^−$ calc 975.13858, found 975.13882.

residue was washed with Et$_2$O. The complex has a R$_f$=0.57 in a TLC (dichloromethane/MeOH 10:1). The product was purified by chromatography column (silica) using dichloromethane/MeOH (gradient 10:1 to 5:1). Yield: 25%

NMR: $^1$H NMR (300 MHz, DMSO-d$_6$) δ 9.22-89.17 (t, J=6.0 Hz, 2H), 8.86-8.80 (t, J=9.0 Hz, 2H), 8.66-8.60 (t, J=6.0 Hz, 2H), 8.53-8.48 (m, 2H), 8.40-8.38 (m, 2H), 8.11-7.99 (m, 6H), 7.62-7.59 (d, J=9.0 Hz, 2H), 7.52-7.46 (t, J=9.0 Hz, 2H), 7.38-7.34 (t, J=6.0 Hz, 2H), 7.29-7.24 (t, J=9.0 Hz, 2H), 7.13-7.09 (m, 2H), 6.90-6.85 (m, 2H), 6.90-6.85 (m, 2H), 6.88-6.75 (t, J=9.0 Hz, 2H), 2.21-2.17 (m, 2H), 1.83-1.77 (m, 2H), 1.55-1.42 (m, 2H).

MS [ESI-MS(+)]: [M]$^+$ calc 957.27936, found 957.27754.

The invention claimed is:

1. An iridium-based chemiluminescent compound of Formula I

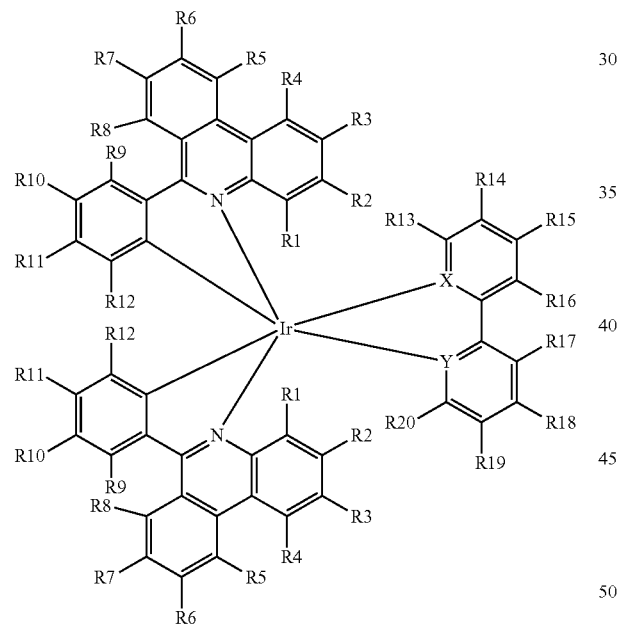

wherein each R1-R20 independently is hydrogen, halide, cyano- or nitro-group, amino, substituted amino, alkylamino, substituted alkylamino, arylamino, substituted arylamino, alkylammonium, substituted alkylammonium, carboxy, carboxylate, carboxylic acid ester, carbamoyl, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl, sulfoxide, phosphono, hydroxyphosphinoyl, hydroxy-alkyl-phosphinoyl, phosphonate, phosphinate or R21, wherein R21 is aryl, substituted aryl, alkyl, substituted alkyl, branched alkyl, substituted branched alkyl, arylalkyl, substituted arylalkyl, alkylaryl, substituted alkylaryl, alkenyl, substituted alkenyl, alkynyl, substituted alkynyl, amino-alkyl, substituted amino-alkyl, aminoalkoxy, substituted amino-alkoxy, amino-aryl, substituted amino-aryl, amino-aryloxy, substituted amino-aryloxy, wherein within R1-R12, or/and within R13-R16 or/and within R17-R20, respectively, two adjacent Rs can form an aromatic ring or a substituted aromatic ring, wherein the substituent is selected from hydrogen, alkyl, substituted alkyl, halide, cyano- or nitro-group, a hydrophilic group, like amino, substituted amino, alkylamino, substituted alkylamino, alkylammonium, substituted alkylammonium, carboxy, carboxylate, carboxylic acid ester, carbamoyl, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl, sulfoxide, phosphono, hydroxyphosphinoyl, hydroxyl-alkyl-phosphinoyl, phosphonate, phosphinate or, wherein within R1-R12, or/and within R13-R16, or/and within R17-R20, respectively, two adjacent Rs can form an aliphatic ring or a substituted aliphatic ring, wherein the substituent is selected from hydrogen, alkyl, substituted alkyl, halide, cyano- or nitro-group, a hydrophilic group, like amino, substituted amino, alkylamino, substituted alkylamino, alkylammonium, substituted alkylammonium, carboxy, carboxylate, carboxylic acid ester, carbamoyl, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl, sulfoxide, phosphono, hydroxyphosphinoyl, hydroxyl-alkyl-phosphinoyl, phosphonate, phosphinate, wherein, if in any of R1-R21 a substitution is present, the substituent in R1-R21 is each independently selected from a halide, cyano- or nitro-group, a hydrophilic group, like an amino, alkylamino, alkylammonium, carboxy, carboxylate, carboxylic acid ester, carbamoyl, hydroxy, alkyloxy, arylalkyloxy, aryloxy, alkylaryloxy, polyethylenoxy, polypropylenoxy, sulfanyl, alkylsulfonyl, arylsulfonyl, sulfo, sulfino, sulfeno, sulfonate, sulfinate, sulfenate, sulfamoyl, sulfoxide, phosphono, hydroxyphosphinoyl, hydroxyl-alkyl-phosphinoyl, phosphonate, phosphinate, wherein alkyl as used herein is a linear or branched alkyl chain with a length of 1-20 carbon atoms or a heteroalkyl chain with the length of 1-20 atoms comprising 1-4 heteroatoms selected from O, N, P, and S, wherein aryl is a 5, 6, or 7 member aryl ring system, or a 5, 6, or 7 member heteroaryl ring system comprising 1-3 heteroatoms selected from O, S and N, wherein at least one of R13-R20 is -Q-Z, wherein Q is a linker or a covalent bond, and wherein Z is a functional group and, wherein at least one of X and Y is N and the other X or Y independently is N or C.

2. The compound according to claim 1, wherein Q is a covalent bond or has as a backbone a straight or branched saturated, unsaturated, unsubstituted or substituted C1-C200 alkyl chain, or a 1 to 200 atom chain consisting of carbon atoms, substituted carbon atoms and/or one or more atoms selected from O, N, P and S, or substituted N, P, S atoms, or a chain as described before with the backbone containing one or more cyclic or heterocyclic aromatic or non-aromatic ring systems.

3. The compound according to claim 2, wherein Q is a covalent bond or has as a backbone a straight or branched saturated, unsaturated, unsubstituted or substituted C1-C100 alkyl chain, or a 1 to 100 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

4. The compound according to claim 3, wherein Q is a covalent bond or has as a backbone a straight or branched saturated, unsaturated, unsubstituted or substituted C1-050 alkyl chain, or a 1 to 50 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

5. The compound according to claim 1, wherein Q is a covalent bond or has as a backbone a straight or branched saturated, unsaturated, unsubstituted or substituted C1-C20 alkyl chain, or a 1 to 20 atom chain consisting of carbon atoms, substituted carbon atoms and/or one or more atoms selected from O, N and S, or a chain as described before with the backbone containing one or more cyclic or heterocyclic aromatic or non-aromatic ring systems.

6. The compound according claim 1, wherein the functional group Z is selected from the group consisting of aldehyde, carboxylic acid, carboxylic acid ester, epoxide, N-hydroxysuccinimide ester, amino group, halogen, hydrazine, hydroxyl, sulfhydryl, maleimido, alkynyl, azide, isocyanate, isothiocyanate and phosphoramidite.

7. A conjugate comprising a compound according claim 1 covalently bound to an affinity binding agent.

8. The conjugate of claim 7, wherein the affinity binding agent is selected from the group consisting of antigen and antibody, biotin or biotin analogue and avidin or streptavidin, sugar and lectin, nucleic acid or nucleic acid analogue and complementary nucleic acid and receptor and ligand.

9. The conjugate according to claim 7, wherein said affinity binding agent is a nucleic acid or an antibody.

10. A method for measuring an analyte by an in vitro method, the method comprising the steps of
a) providing a sample suspected or known to comprise the analyte,
b) contacting said sample with a conjugate according to any of claims 7 to 9 under conditions appropriate for formation of an analyte conjugate complex, and
c) measuring the complex formed in step (b) and thereby obtaining a measure of the analyte.

11. A compound according to Formula II

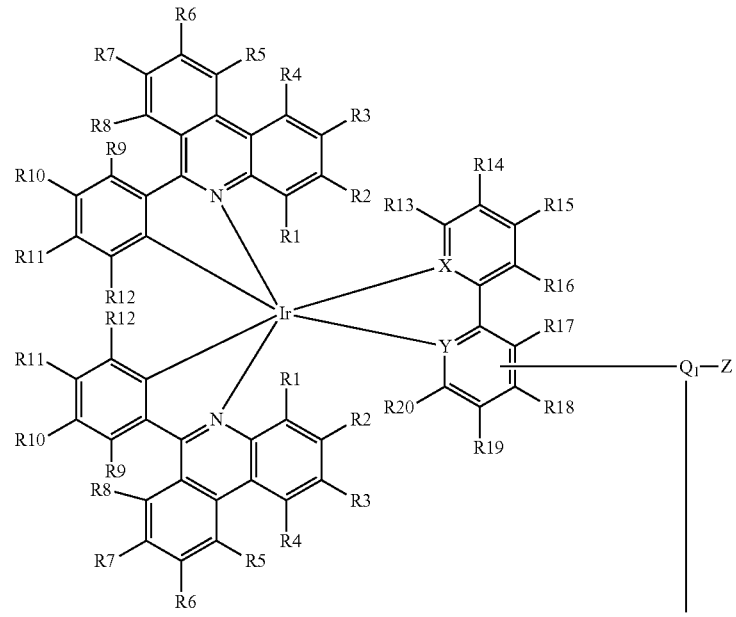

(FORMULA I (a))

-continued

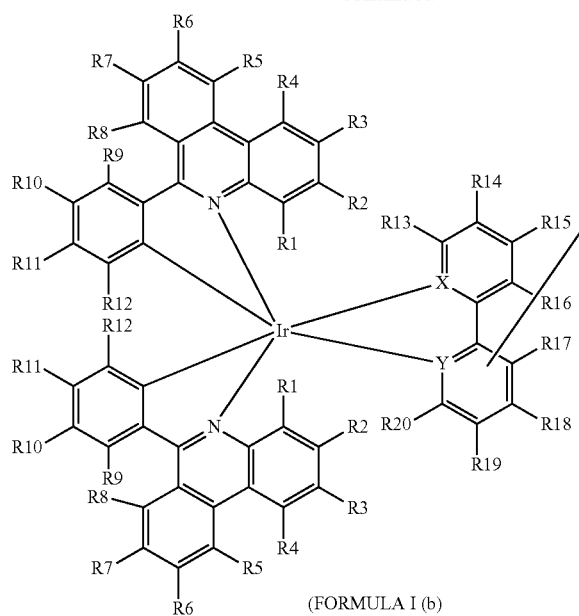

(FORMULA I (b))

wherein R1 to R20 are as defined for Formula I in claim 1 with the exception that Q of Formula I is Q1 or Q2 in Formula II, respectively, wherein Q1 is a linker, wherein at least one of R13-R20 in Formula I (b) is Q2 and each Q2 independently is a linker or a covalent bond, wherein (n) is an integer from 1 to 50, wherein X and Y are as defined for Formula I, and wherein Z is a functional group.

* * * * *

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial
<220> FEATURE:
<223> OTHER INFORMATION: Not derived from a naturally-occurring sequence
<220> FEATURE:
<221> NAME/KEY: MISC_FEATURE
<222> LOCATION: (2)..(6)
<223> OTHER INFORMATION: This residue is beta alanine
<220> FEATURE:
<221> NAME/KEY: MISC_FEATURE
<222> LOCATION: (8)..(12)
<223> OTHER INFORMATION: This residue is beta alanine

<400> SEQUENCE: 1

Lys Xaa Xaa Xaa Xaa Xaa Lys Xaa Xaa Xaa Xaa Xaa
1               5                  10
```